United States Patent
Al-Ali

(10) Patent No.: US 9,795,300 B2
(45) Date of Patent: *Oct. 24, 2017

(54) WEARABLE PORTABLE PATIENT MONITOR

(71) Applicant: MASIMO CORPORATION, Irvine, CA (US)

(72) Inventor: Ammar Al-Ali, San Juan Capistrano, CA (US)

(73) Assignee: MASIMO CORPORATION, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/499,716

(22) Filed: Apr. 27, 2017

(65) Prior Publication Data

US 2017/0224216 A1    Aug. 10, 2017

Related U.S. Application Data

(63) Continuation of application No. 15/448,989, filed on Mar. 3, 2017, which is a continuation of application
(Continued)

(51) Int. Cl.
*A61B 5/1455* (2006.01)
*A61B 5/0205* (2006.01)
(Continued)

(52) U.S. Cl.
CPC ............ *A61B 5/0024* (2013.01); *A61B 5/021* (2013.01); *A61B 5/0205* (2013.01);
(Continued)

(58) Field of Classification Search
CPC ... A61B 5/0002; A61B 5/0004; A61B 5/0024; A61B 5/02; A61B 5/0205; A61B 5/0402;
(Continued)

(56) References Cited

U.S. PATENT DOCUMENTS 3,646,606 A    2/1972    Buxton et al.
3,690,313 A    9/1972    Weppner et al.
(Continued)

FOREIGN PATENT DOCUMENTS

EP    0602459    6/1994
EP    0 735 499    10/1996
(Continued)

OTHER PUBLICATIONS

US 8,845,543, 09/2014, Diab et al. (withdrawn)
(Continued)

*Primary Examiner* — Eric Winakur
(74) *Attorney, Agent, or Firm* — Knobbe Martens; Olson & Bear LLP

(57) ABSTRACT

A wearable, portable physiological monitor configured to wirelessly transmit real time information regarding a plurality physiological parameters. The portable monitor includes a plurality of sensor ports, where at least a first sensor port is positioned on a side of a housing of the portable monitor such that, when the portable monitor is attached to an arm of a patient, a wired connection extending from the first sensor port to a first physiological sensor positioned on a digit of the patient follows a path to the digit of the patient that avoids tangling of the wired connection. The portable monitor further includes one or more processing devices configured to cause display of parameter values, combine information indicative of the signals into a single word or bit stream, and encode and generate a baseband signal. Further includes a transmitter to modulate the baseband signal and wirelessly transmit.

20 Claims, 17 Drawing Sheets

Related U.S. Application Data

No. 14/815,232, filed on Jul. 31, 2015, now abandoned, which is a continuation of application No. 14/217,788, filed on Mar. 18, 2014, now Pat. No. 9,113,832, which is a continuation of application No. 14/037,137, filed on Sep. 25, 2013, now Pat. No. 9,113,831, which is a continuation of application No. 12/955,826, filed on Nov. 29, 2010, now Pat. No. 8,548,548, which is a continuation of application No. 11/417,006, filed on May 3, 2006, now Pat. No. 7,844,315, which is a continuation of application No. 11/048,330, filed on Feb. 1, 2005, now Pat. No. 7,844,314, which is a continuation of application No. 10/377,933, filed on Feb. 28, 2003, now Pat. No. 6,850,788.

(60) Provisional application No. 60/367,428, filed on Mar. 25, 2002.

(51) Int. Cl.
*A61B 5/00* (2006.01)
*A61B 5/021* (2006.01)
*A61B 5/0428* (2006.01)
*G08B 21/04* (2006.01)
*H04W 4/00* (2009.01)

(52) U.S. Cl.
CPC ........ *A61B 5/0428* (2013.01); *A61B 5/14552* (2013.01); *A61B 5/6824* (2013.01); *A61B 5/6831* (2013.01); *A61B 5/7228* (2013.01); *A61B 5/7425* (2013.01); *A61B 5/7445* (2013.01); *A61B 5/7475* (2013.01); *G08B 21/0453* (2013.01); *A61B 2562/222* (2013.01); *A61B 2562/227* (2013.01); *H04W 4/005* (2013.01)

(58) Field of Classification Search
CPC . A61B 5/1455; A61B 5/14551; A61B 5/6825; A61B 5/6826; A61B 5/6831; A61B 5/72; A61B 2560/0043; A61B 2562/06
See application file for complete search history.

(56) References Cited

U.S. PATENT DOCUMENTS

| | | |
|---|---|---|
| 3,810,102 A | 5/1974 | Parks, III et al. |
| 3,815,583 A | 6/1974 | Scheidt |
| 3,972,320 A | 8/1976 | Kalman |
| 3,978,849 A | 9/1976 | Geneen |
| 4,013,067 A | 3/1977 | Kresse et al. |
| 4,108,166 A | 8/1978 | Schmid |
| 4,231,354 A | 11/1980 | Kurtz et al. |
| 4,589,415 A | 5/1986 | Haaga |
| 4,662,378 A | 5/1987 | Thomis |
| 4,773,422 A | 9/1988 | Isaacson et al. |
| 4,838,275 A | 6/1989 | Lee |
| 4,852,570 A | 8/1989 | Levine |
| 4,960,128 A | 10/1990 | Gordon et al. |
| 4,964,408 A | 10/1990 | Hink et al. |
| RE33,643 E | 7/1991 | Isaacson et al. |
| 5,041,187 A | 8/1991 | Hink et al. |
| 5,069,213 A | 12/1991 | Polczynski |
| 5,090,410 A | 2/1992 | Saper et al. |
| 5,092,340 A | 3/1992 | Yamaguchi et al. |
| 5,140,519 A | 8/1992 | Friesdorf et al. |
| 5,159,932 A | 11/1992 | Zanetti et al. |
| 5,161,539 A | 11/1992 | Evans et al. |
| 5,163,438 A | 11/1992 | Gordon et al. |
| 5,203,342 A | 4/1993 | Sakai |
| 5,262,944 A | 11/1993 | Weisner et al. |
| 5,277,189 A | 1/1994 | Jacobs |
| 5,278,627 A | 1/1994 | Aoyagi et al. |
| 5,282,474 A | 2/1994 | Valdes Sosa et al. |
| 5,296,688 A | 3/1994 | Hamilton et al. |
| 5,318,037 A | 6/1994 | Evans et al. |
| 5,319,355 A | 6/1994 | Russek |
| 5,331,549 A | 7/1994 | Crawford, Jr. |
| 5,333,106 A | 7/1994 | Lanpher et al. |
| 5,337,744 A | 8/1994 | Branigan |
| 5,341,805 A | 8/1994 | Stavridi et al. |
| 5,348,008 A | 9/1994 | Bornn et al. |
| 5,358,519 A | 10/1994 | Grandjean |
| D353,195 S | 12/1994 | Savage et al. |
| D353,196 S | 12/1994 | Savage et al. |
| 5,375,599 A | 12/1994 | Shimizu |
| 5,375,604 A | 12/1994 | Kelly et al. |
| 5,377,676 A | 1/1995 | Vari et al. |
| 5,392,777 A | 2/1995 | Swedlow et al. |
| 5,400,794 A | 3/1995 | Gorman |
| D357,982 S | 5/1995 | Dahl et al. |
| 5,416,695 A | 5/1995 | Stutman et al. |
| 5,417,222 A | 5/1995 | Dempsey et al. |
| D359,546 S | 6/1995 | Savage et al. |
| 5,431,170 A | 7/1995 | Mathews |
| 5,434,611 A | 7/1995 | Tamura |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,483,968 A | 1/1996 | Adam et al. |
| 5,490,505 A | 2/1996 | Diab et al. |
| 5,490,523 A | 2/1996 | Isaacson et al. |
| 5,494,041 A | 2/1996 | Wilk |
| 5,494,043 A | 2/1996 | O'Sullivan et al. |
| 5,503,149 A | 4/1996 | Beavin |
| 5,505,202 A | 4/1996 | Mogi et al. |
| 5,511,553 A | 4/1996 | Segalowitz |
| 5,533,511 A | 7/1996 | Kaspari et al. |
| 5,534,851 A | 7/1996 | Russek |
| 5,537,289 A | 7/1996 | Dahl |
| 5,544,649 A | 8/1996 | David et al. |
| 5,553,609 A | 9/1996 | Chen et al. |
| 5,558,638 A | 9/1996 | Evers et al. |
| 5,561,275 A | 10/1996 | Savage et al. |
| 5,562,002 A | 10/1996 | Lalin |
| 5,566,676 A | 10/1996 | Rosenfeldt et al. |
| 5,576,952 A | 11/1996 | Stutman et al. |
| 5,579,001 A | 11/1996 | Dempsey et al. |
| 5,584,296 A | 12/1996 | Cui et al. |
| 5,590,649 A | 1/1997 | Caro et al. |
| 5,602,924 A | 2/1997 | Durand et al. |
| 5,619,991 A | 4/1997 | Sloane |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,640,967 A | 6/1997 | Fine et al. |
| 5,645,440 A | 7/1997 | Tobler et al. |
| 5,658,316 A | 8/1997 | Lamond et al. |
| 5,673,692 A | 10/1997 | Schulze et al. |
| 5,685,299 A | 11/1997 | Diab et al. |
| 5,685,314 A | 11/1997 | Geheb et al. |
| 5,687,717 A | 11/1997 | Halpern et al. |
| 5,694,020 A | 12/1997 | Lang et al. |
| 5,724,580 A | 3/1998 | Levin et al. |
| 5,724,983 A | 3/1998 | Selker et al. |
| 5,725,308 A | 3/1998 | Smith et al. |
| 5,734,739 A | 3/1998 | Sheehan et al. |
| D393,830 S | 4/1998 | Tobler et al. |
| 5,743,262 A | 4/1998 | Lepper, Jr. et al. |
| 5,746,697 A | 5/1998 | Swedlow et al. |
| 5,758,079 A | 5/1998 | Ludwig et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,772,585 A | 6/1998 | Lavin et al. |
| 5,779,631 A | 7/1998 | Chance |
| 5,782,757 A | 7/1998 | Diab et al. |

(56) References Cited

U.S. PATENT DOCUMENTS

| | | |
|---|---|---|
| 5,782,805 A | 7/1998 | Meinzer |
| 5,785,659 A | 7/1998 | Caro et al. |
| 5,791,347 A | 8/1998 | Flaherty et al. |
| 5,792,052 A | 8/1998 | Isaacson et al. |
| 5,800,349 A | 9/1998 | Isaacson et al. |
| 5,801,637 A | 9/1998 | Lomholt |
| 5,810,734 A | 9/1998 | Caro et al. |
| 5,813,403 A | 9/1998 | Soller et al. |
| 5,822,544 A | 10/1998 | Chaco et al. |
| 5,822,546 A | 10/1998 | George |
| 5,823,950 A | 10/1998 | Diab et al. |
| 5,829,723 A | 11/1998 | Brunner |
| 5,830,131 A | 11/1998 | Caro et al. |
| 5,830,137 A | 11/1998 | Scharf |
| 5,833,618 A | 11/1998 | Caro et al. |
| RE36,000 E | 12/1998 | Swedlow et al. |
| 5,855,550 A | 1/1999 | Lai et al. |
| 5,860,919 A | 1/1999 | Kiani-Azarbayjany et al. |
| 5,865,736 A | 2/1999 | Baker et al. |
| 5,876,351 A | 3/1999 | Rohde |
| 5,879,292 A | 3/1999 | Sternberg et al. |
| 5,890,929 A | 4/1999 | Mills et al. |
| 5,904,654 A | 5/1999 | Wohltmann et al. |
| 5,910,139 A | 6/1999 | Cochran et al. |
| 5,919,134 A | 7/1999 | Diab |
| 5,921,920 A | 7/1999 | Marshall et al. |
| 5,924,074 A | 7/1999 | Evans |
| 5,931,160 A | 8/1999 | Gilmore et al. |
| 5,931,791 A | 8/1999 | Saltzstein et al. |
| 5,934,925 A | 8/1999 | Tobler et al. |
| 5,940,182 A | 8/1999 | Lepper, Jr. et al. |
| 5,942,986 A | 8/1999 | Shabot et al. |
| 5,957,854 A | 9/1999 | Besson et al. |
| 5,987,519 A | 11/1999 | Peifer et al. |
| 5,995,855 A | 11/1999 | Kiani et al. |
| 5,997,343 A | 12/1999 | Mills et al. |
| 6,002,952 A | 12/1999 | Diab et al. |
| 6,006,119 A | 12/1999 | Soller et al. |
| 6,011,985 A | 1/2000 | Athan et al. |
| 6,011,986 A | 1/2000 | Diab et al. |
| 6,014,346 A | 1/2000 | Malone |
| 6,018,673 A | 1/2000 | Chin et al. |
| 6,024,699 A | 2/2000 | Surwit et al. |
| 6,027,452 A | 2/2000 | Flaherty et al. |
| 6,032,678 A | 3/2000 | Rottem |
| 6,035,230 A | 3/2000 | Kang et al. |
| 6,036,642 A | 3/2000 | Diab et al. |
| 6,036,718 A | 3/2000 | Ledford et al. |
| 6,045,509 A | 4/2000 | Caro et al. |
| 6,045,527 A | 4/2000 | Appelbaum et al. |
| 6,057,758 A | 5/2000 | Dempsey et al. |
| 6,067,462 A | 5/2000 | Diab et al. |
| 6,081,735 A | 6/2000 | Diab et al. |
| 6,088,607 A | 7/2000 | Diab et al. |
| 6,090,056 A | 7/2000 | Bystrom et al. |
| 6,093,146 A | 7/2000 | Filangeri |
| 6,101,478 A | 8/2000 | Brown |
| 6,106,463 A | 8/2000 | Wilk |
| 6,110,522 A | 8/2000 | Lepper, Jr. et al. |
| 6,124,597 A | 9/2000 | Shehada |
| 6,128,521 A | 10/2000 | Marro et al. |
| 6,129,675 A | 10/2000 | Jay |
| 6,132,218 A | 10/2000 | Benja-Athon |
| 6,139,494 A | 10/2000 | Cairnes |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,154,667 A | 11/2000 | Miura et al. |
| 6,157,850 A | 12/2000 | Diab et al. |
| 6,165,005 A | 12/2000 | Mills et al. |
| 6,167,258 A | 12/2000 | Schmidt et al. |
| D437,058 S | 1/2001 | Gozani |
| 6,168,563 B1 | 1/2001 | Brown |
| 6,171,237 B1 | 1/2001 | Avitall et al. |
| 6,175,752 B1 | 1/2001 | Say et al. |
| 6,178,343 B1 | 1/2001 | Bindszus et al. |
| 6,183,417 B1 | 2/2001 | Gehab et al. |
| 6,184,521 B1 | 2/2001 | Coffin, IV et al. |
| 6,185,448 B1 | 2/2001 | Borovsky |
| 6,190,327 B1 | 2/2001 | Isaacson et al. |
| 6,195,576 B1 | 2/2001 | John |
| 6,206,830 B1 | 3/2001 | Diab et al. |
| 6,215,403 B1 | 4/2001 | Chan et al. |
| 6,221,012 B1 | 4/2001 | Maschke et al. |
| 6,224,553 B1 | 5/2001 | Nevo |
| 6,229,856 B1 | 5/2001 | Diab et al. |
| 6,230,142 B1 | 5/2001 | Benigno et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,241,684 B1 * | 6/2001 | Amano ............ A61B 5/02438 600/503 |
| 6,251,113 B1 | 6/2001 | Appelbaum |
| 6,253,097 B1 | 6/2001 | Aronow et al. |
| 6,256,523 B1 | 7/2001 | Diab et al. |
| 6,263,222 B1 | 7/2001 | Diab et al. |
| 6,267,723 B1 | 7/2001 | Matsumura et al. |
| 6,269,262 B1 | 7/2001 | Kandori et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,289,238 B1 | 9/2001 | Besson et al. |
| 6,301,493 B1 | 10/2001 | Marro et al. |
| 6,304,767 B1 | 10/2001 | Soller et al. |
| 6,312,378 B1 | 11/2001 | Bardy |
| 6,317,627 B1 | 11/2001 | Ennen et al. |
| 6,321,100 B1 | 11/2001 | Parker |
| 6,322,502 B1 | 11/2001 | Schoenberg et al. |
| 6,325,761 B1 | 12/2001 | Jay |
| 6,329,139 B1 | 12/2001 | Nova et al. |
| 6,334,065 B1 | 12/2001 | Al-Ali et al. |
| 6,338,039 B1 | 1/2002 | Lonski et al. |
| 6,343,224 B1 | 1/2002 | Parker |
| 6,349,228 B1 | 2/2002 | Kiani et al. |
| 6,352,504 B1 | 3/2002 | Ise |
| 6,354,235 B1 | 3/2002 | Davies |
| 6,360,114 B1 | 3/2002 | Diab et al. |
| 6,364,834 B1 | 4/2002 | Reuss et al. |
| 6,364,839 B1 | 4/2002 | Little et al. |
| 6,368,283 B1 | 4/2002 | Xu et al. |
| 6,371,921 B1 | 4/2002 | Caro et al. |
| 6,374,129 B1 | 4/2002 | Chin et al. |
| 6,377,829 B1 | 4/2002 | Al-Ali |
| 6,385,476 B1 | 5/2002 | Osadchy et al. |
| 6,385,589 B1 | 5/2002 | Trusheim et al. |
| 6,387,039 B1 | 5/2002 | Moses |
| 6,388,240 B2 | 5/2002 | Schulz et al. |
| 6,397,091 B2 | 5/2002 | Diab et al. |
| 6,405,083 B1 | 6/2002 | Rockwell et al. |
| 6,407,335 B1 | 6/2002 | Franklin-Lees |
| 6,430,437 B1 | 8/2002 | Marro |
| 6,430,525 B1 | 8/2002 | Weber et al. |
| 6,440,067 B1 | 8/2002 | Deluca et al. |
| 6,454,708 B1 | 9/2002 | Ferguson et al. |
| 6,463,311 B1 | 10/2002 | Diab |
| 6,470,199 B1 | 10/2002 | Kopotic et al. |
| 6,470,893 B1 | 10/2002 | Boesen |
| 6,491,647 B1 | 12/2002 | Bridger et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,516,289 B2 * | 2/2003 | David ............. A61B 5/04085 600/300 |
| 6,519,487 B1 | 2/2003 | Parker |
| 6,524,240 B1 | 2/2003 | Thede |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,544,173 B2 | 4/2003 | West et al. |
| 6,544,174 B2 | 4/2003 | West et al. |
| 6,551,243 B2 | 4/2003 | Bocionek et al. |
| 6,553,242 B1 | 4/2003 | Sarussi |
| 6,577,893 B1 | 6/2003 | Besson et al. |

(56) References Cited

U.S. PATENT DOCUMENTS

| | | |
|---|---|---|
| 6,578,428 B1 | 6/2003 | Dromms et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,612,984 B1 | 9/2003 | Kerr, II |
| 6,616,606 B1 | 9/2003 | Peterson et al. |
| 6,632,181 B2 | 10/2003 | Flaherty et al. |
| 6,639,668 B1 | 10/2003 | Trepagnier |
| 6,640,116 B2 | 10/2003 | Diab |
| 6,641,533 B2 | 11/2003 | Causey et al. |
| 6,643,530 B2 | 11/2003 | Diab et al. |
| 6,646,556 B1 | 11/2003 | Smith et al. |
| 6,650,917 B2 | 11/2003 | Diab et al. |
| 6,650,939 B2 | 11/2003 | Takpke, II et al. |
| 6,654,624 B2 | 11/2003 | Diab et al. |
| D483,872 S | 12/2003 | Cruz et al. |
| 6,658,276 B2 | 12/2003 | Kianl et al. |
| 6,661,161 B1 | 12/2003 | Lanzo et al. |
| 6,663,570 B2 | 12/2003 | Mott et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,694,160 B2 | 2/2004 | Chin |
| 6,694,180 B1 | 2/2004 | Boesen |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,719,694 B2 | 4/2004 | Weng et al. |
| 6,720,734 B2 | 4/2004 | Norris |
| 6,721,582 B2 | 4/2004 | Trepagnier et al. |
| 6,721,585 B1 | 4/2004 | Parker |
| 6,725,075 B2 | 4/2004 | Al-Ali |
| 6,725,086 B2 | 4/2004 | Marinello |
| 6,728,560 B2 | 4/2004 | Kollias et al. |
| 6,731,962 B1 | 5/2004 | Katarow et al. |
| 6,735,459 B2 | 5/2004 | Parker |
| 6,745,060 B2 | 6/2004 | Diab et al. |
| 6,746,406 B2 | 6/2004 | Lia et al. |
| 6,750,463 B1 | 6/2004 | Riley |
| 6,751,492 B2 | 6/2004 | Ben-haim |
| 6,760,607 B2 | 7/2004 | Al-Ali |
| 6,766,188 B2 | 7/2004 | Soller |
| 6,770,028 B1 | 8/2004 | Ali et al. |
| 6,771,994 B2 | 8/2004 | Kiani et al. |
| 6,783,492 B2 | 8/2004 | Dominguez |
| 6,790,178 B1 | 9/2004 | Mault et al. |
| 6,792,300 B1 | 9/2004 | Diab et al. |
| 6,795,724 B2 | 9/2004 | Hogan |
| 6,796,186 B2 | 9/2004 | Lia et al. |
| 6,804,656 B1 | 10/2004 | Rosenfeld |
| 6,807,050 B1 | 10/2004 | Whitehorn et al. |
| 6,813,511 B2 | 11/2004 | Diab et al. |
| 6,816,741 B2 | 11/2004 | Diab |
| 6,817,979 B2 | 11/2004 | Nihtila et al. |
| 6,822,564 B2 | 11/2004 | Al-Ali |
| 6,826,419 B2 | 11/2004 | Diab et al. |
| 6,830,711 B2 | 12/2004 | Mills et al. |
| 6,837,848 B2 | 1/2005 | Bonner et al. |
| 6,841,535 B2 | 1/2005 | Divita et al. |
| 6,845,256 B2 | 1/2005 | Chin et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,855,112 B2 | 2/2005 | Kao et al. |
| 6,860,266 B2 | 3/2005 | Blike |
| 6,861,639 B2 | 3/2005 | Al-Ali |
| 6,897,788 B2 | 5/2005 | Khair et al. |
| 6,898,452 B2 | 5/2005 | Al-Ali et al. |
| 6,907,237 B1 | 6/2005 | Dorenbosch et al. |
| 6,915,149 B2 | 7/2005 | Ben-haim |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,942,616 B2 | 9/2005 | Kerr, II |
| 6,943,348 B1 | 9/2005 | Coffin, IV |
| 6,950,687 B2 | 9/2005 | Al-Ali |
| 6,952,340 B2 | 10/2005 | Son |
| 6,961,598 B2 | 11/2005 | Diab |
| 6,970,792 B1 | 11/2005 | Diab |
| 6,979,812 B2 | 12/2005 | Al-Ali |
| 6,980,419 B2 | 12/2005 | Smith et al. |
| 6,983,179 B2 | 1/2006 | Ben-haim |
| 6,985,764 B2 | 1/2006 | Mason et al. |
| 6,988,989 B2 | 1/2006 | Weiner et al. |
| 6,990,087 B2 | 1/2006 | Rao et al. |
| 6,993,371 B2 | 1/2006 | Kiani et al. |
| 6,996,427 B2 | 2/2006 | Ali et al. |
| 6,997,884 B2 | 2/2006 | Ulmsten |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,025,729 B2 | 4/2006 | De Chazal et al. |
| 7,027,849 B2 | 4/2006 | Al-Ali |
| 7,030,749 B2 | 4/2006 | Al-Ali |
| 7,033,761 B2 | 4/2006 | Shafer |
| 7,035,686 B2 | 4/2006 | Hogan |
| 7,039,449 B2 | 5/2006 | Al-Ali |
| 7,041,060 B2 | 5/2006 | Flaherty et al. |
| 7,044,918 B2 | 5/2006 | Diab |
| 7,044,930 B2 | 5/2006 | Stromberg |
| 7,063,666 B2 | 6/2006 | Weng et al. |
| 7,067,893 B2 | 6/2006 | Mills et al. |
| 7,079,035 B2 | 7/2006 | Bock et al. |
| 7,096,052 B2 | 8/2006 | Mason et al. |
| 7,096,054 B2 | 8/2006 | Abdul-Hafiz et al. |
| 7,125,382 B2 | 10/2006 | Zhou et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,188,621 B2 | 3/2007 | DeVries et al. |
| 7,190,261 B2 | 3/2007 | Al-Ali |
| 7,208,119 B1 | 4/2007 | Kurtock et al. |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,229,415 B2 | 6/2007 | Schwartz |
| 7,239,905 B2 | 7/2007 | Kiani-Azarbayjany et al. |
| 7,241,287 B2 | 7/2007 | Shehada et al. |
| 7,244,251 B2 | 7/2007 | Shehada et al. |
| 7,245,373 B2 | 7/2007 | Soller et al. |
| 7,245,953 B1 | 7/2007 | Parker |
| 7,252,659 B2 | 8/2007 | Shehada et al. |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,256,708 B2 | 8/2007 | Rosenfeld |
| 7,257,438 B2 | 8/2007 | Kinast |
| 7,261,697 B2 | 8/2007 | Berstein |
| 7,264,616 B2 | 9/2007 | Shehada et al. |
| 7,267,671 B2 | 9/2007 | Shehada et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,285,090 B2 | 10/2007 | Stivoric |
| 7,289,835 B2 | 10/2007 | Mansfield et al. |
| 7,292,883 B2 | 11/2007 | De Felice et al. |
| 7,295,866 B2 | 11/2007 | Al-Ali |

(56) References Cited

U.S. PATENT DOCUMENTS

| | | |
|---|---|---|
| 7,307,543 B2 | 12/2007 | Rosenfeld |
| 7,313,423 B2 | 12/2007 | Griffin et al. |
| 7,314,446 B2 | 1/2008 | Byrd et al. |
| 7,315,825 B2 | 1/2008 | Rosenfeld |
| 7,321,862 B2 | 1/2008 | Rosenfeld |
| 7,322,971 B2 | 1/2008 | Shehada et al. |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,178 B2 | 4/2008 | Ziel et al. |
| 7,356,365 B2 | 4/2008 | Schurman |
| 7,359,742 B2 | 4/2008 | Maser et al. |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,378,975 B1 | 5/2008 | Smith et al. |
| 7,382,247 B2 | 6/2008 | Welch et al. |
| 7,383,070 B2 | 6/2008 | Diab et al. |
| 7,390,299 B2 | 6/2008 | Weiner et al. |
| 7,392,074 B2 | 6/2008 | Isaacson et al. |
| 7,395,216 B2 | 7/2008 | Rosenfeld |
| 7,411,509 B2 | 8/2008 | Rosenfeld |
| 7,413,546 B2 | 8/2008 | Agutter et al. |
| 7,415,297 B2 | 8/2008 | Al-Ali et al. |
| 7,419,483 B2 | 9/2008 | Shehada |
| 7,428,432 B2 | 9/2008 | Ali et al. |
| 7,433,827 B2 | 10/2008 | Rosenfeld |
| 7,438,683 B2 | 10/2008 | Al-Ali et al. |
| 7,439,856 B2 | 10/2008 | Weiner et al. |
| 7,440,787 B2 | 10/2008 | Diab |
| 7,454,240 B2 | 11/2008 | Diab et al. |
| 7,454,359 B2 | 11/2008 | Rosenfeld |
| 7,454,360 B2 | 11/2008 | Rosenfeld |
| 7,462,151 B2 | 12/2008 | Childre et al. |
| 7,467,002 B2 | 12/2008 | Weber et al. |
| 7,467,094 B2 | 12/2008 | Rosenfeld |
| 7,469,157 B2 | 12/2008 | Diab et al. |
| 7,471,969 B2 | 12/2008 | Diab et al. |
| 7,471,971 B2 | 12/2008 | Diab et al. |
| 7,475,019 B2 | 1/2009 | Rosenfeld |
| 7,483,729 B2 | 1/2009 | Al-Ali et al. |
| 7,483,730 B2 | 1/2009 | Diab et al. |
| 7,486,977 B2 | 2/2009 | Sweitzer et al. |
| 7,489,250 B2 | 2/2009 | Bock et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,497,828 B1 | 3/2009 | Wilk et al. |
| 7,499,739 B2 | 3/2009 | Sweitzer et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,515,043 B2 | 4/2009 | Welch et al. |
| 7,515,044 B2 | 4/2009 | Welch et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,532,919 B2 | 5/2009 | Soyemi et al. |
| 7,549,961 B1 | 6/2009 | Hwang |
| 7,551,717 B2 | 6/2009 | Tome et al. |
| 7,559,520 B2 | 7/2009 | Quijano et al. |
| 7,563,110 B2 | 7/2009 | Al-Ali et al. |
| 7,577,475 B2 | 8/2009 | Consentino et al. |
| 7,590,950 B2 | 9/2009 | Collins et al. |
| 7,596,398 B2 | 9/2009 | Al-Ali et al. |
| 7,597,665 B2 | 10/2009 | Wilk et al. |
| 7,612,999 B2 | 11/2009 | Clark et al. |
| 7,616,303 B2 | 11/2009 | Yang et al. |
| 7,618,375 B2 | 11/2009 | Flaherty |
| D606,659 S | 12/2009 | Kiani et al. |
| 7,639,145 B2 | 12/2009 | Lawson et al. |
| 7,647,083 B2 | 1/2010 | Al-Ali et al. |
| 7,650,291 B2 | 1/2010 | Rosenfeld |
| D609,193 S | 2/2010 | Al-Ali et al. |
| 7,654,966 B2 | 2/2010 | Westinskow et al. |
| 7,684,845 B2 | 3/2010 | Juan |
| 7,689,437 B1 | 3/2010 | Teller et al. |
| RE41,236 E | 4/2010 | Seely |
| D614,305 S | 4/2010 | Al-Ali et al. |
| 7,693,697 B2 | 4/2010 | Westinskow et al. |
| RE41,317 E | 5/2010 | Parker |
| D615,655 S | 5/2010 | Maser et al. |
| 7,722,542 B2 | 5/2010 | Lia et al. |
| 7,729,733 B2 | 6/2010 | Al-Ali et al. |
| 7,734,320 B2 | 6/2010 | Al-Ali |
| 7,736,318 B2 | 6/2010 | Consentino et al. |
| 7,740,590 B2 | 6/2010 | Bernstein |
| 7,761,127 B2 | 7/2010 | Al-Ali et al. |
| 7,761,128 B2 | 7/2010 | Al-Ali et al. |
| 7,763,420 B2 | 7/2010 | Strizker et al. |
| 7,764,982 B2 | 7/2010 | Dalke et al. |
| D621,515 S | 8/2010 | Chua et al. |
| D621,516 S | 8/2010 | Kiani et al. |
| 7,766,818 B2 | 8/2010 | Iketani et al. |
| 7,774,060 B2 | 8/2010 | Westenskow et al. |
| 7,778,851 B2 | 8/2010 | Schoenberg et al. |
| 7,791,155 B2 | 9/2010 | Diab |
| 7,794,407 B2 | 9/2010 | Rothenberg |
| 7,801,581 B2 | 9/2010 | Diab |
| 7,801,605 B2 | 9/2010 | Smirles et al. |
| 7,806,830 B2 | 10/2010 | Bernstein |
| 7,820,184 B2 | 10/2010 | Strizker et al. |
| 7,822,452 B2 | 10/2010 | Schurman et al. |
| RE41,912 E | 11/2010 | Parker |
| 7,831,450 B2 | 11/2010 | Schoenberg |
| 7,841,986 B2 | 11/2010 | He et al. |
| 7,844,313 B2 | 11/2010 | Kiani et al. |
| 7,844,314 B2 | 11/2010 | Al-Ali |
| 7,844,315 B2 | 11/2010 | Al-Ali |
| 7,848,935 B2 | 12/2010 | Gotlib |
| 7,858,322 B2 | 12/2010 | Tymianski et al. |
| 7,865,222 B2 | 1/2011 | Weber et al. |
| 7,865,232 B1 | 1/2011 | Krishnaswamy et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,881,892 B2 | 2/2011 | Soyemi et al. |
| 7,884,314 B2 | 2/2011 | Hamada |
| 7,890,156 B2 | 2/2011 | Ooi et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,914,514 B2 | 3/2011 | Calderon |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,963,927 B2 | 6/2011 | Kelleher et al. |
| 7,967,749 B2 | 6/2011 | Hutchinson et al. |
| 7,970,450 B2 | 6/2011 | Kroecker |
| 7,976,472 B2 | 7/2011 | Kiani |
| 7,988,637 B2 | 8/2011 | Diab |
| 7,988,639 B2 | 8/2011 | Starks |

(56) References Cited

U.S. PATENT DOCUMENTS

| | | |
|---|---|---|
| 7,990,382 B2 | 8/2011 | Kiani |
| 7,991,446 B2 | 8/2011 | Al-Ali et al. |
| 7,991,463 B2 | 8/2011 | Kelleher et al. |
| 7,991,625 B2 | 8/2011 | Rosenfeld |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,027,846 B2 | 9/2011 | Schoenberg |
| 8,028,701 B2 | 10/2011 | Al-Ali et al. |
| 8,029,765 B2 | 10/2011 | Bellott et al. |
| 8,033,996 B2 | 10/2011 | Behar |
| 8,036,727 B2 | 10/2011 | Schurman et al. |
| 8,036,728 B2 | 10/2011 | Diab et al. |
| 8,036,736 B2 | 10/2011 | Snyder et al. |
| 8,038,625 B2 | 10/2011 | Afonso et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| 8,068,104 B2 | 11/2011 | Rampersad |
| 8,073,707 B2 | 12/2011 | Teller et al. |
| 8,094,013 B1 | 1/2012 | Lee et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| D659,836 S | 5/2012 | Bensch et al. |
| 8,170,887 B2 | 5/2012 | Rosenfeld |
| 8,175,672 B2 | 5/2012 | Parker |
| 8,175,895 B2 | 5/2012 | Rosenfeld |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,200,308 B2 | 6/2012 | Zhang et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,206,312 B2 | 6/2012 | Farquhar |
| 8,214,007 B2 | 7/2012 | Baker et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,235,907 B2 | 8/2012 | Wilk et al. |
| 8,239,780 B2 | 8/2012 | Manetta et al. |
| 8,241,213 B2 | 8/2012 | Lynn et al. |
| 8,244,325 B2 | 8/2012 | Al-Ali et al. |
| 8,249,815 B2 | 8/2012 | Taylor |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,294,588 B2 | 10/2012 | Fisher et al. |
| 8,294,716 B2 | 10/2012 | Lord et al. |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,311,747 B2 | 11/2012 | Taylor |
| 8,311,748 B2 | 11/2012 | Taylor et al. |
| 8,315,683 B2 | 11/2012 | Al-Ali et al. |
| 8,315,812 B2 | 11/2012 | Taylor |
| 8,315,813 B2 | 11/2012 | Taylor et al. |
| 8,315,814 B2 | 11/2012 | Taylor et al. |
| 8,321,150 B2 | 11/2012 | Taylor |
| RE43,860 E | 12/2012 | Parker |
| 8,326,392 B2 | 12/2012 | Grubac et al. |
| 8,326,649 B2 | 12/2012 | Rosenfeld |
| 8,328,793 B2 | 12/2012 | Birkenbach et al. |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,360,936 B2 | 1/2013 | Dibenedetto et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,972 B2 | 2/2013 | Bochenko et al. |
| 8,385,995 B2 | 2/2013 | Al-ali et al. |
| 8,385,996 B2 | 2/2013 | Smith et al. |
| D679,018 S | 3/2013 | Fullerton et al. |
| 8,388,353 B2 | 3/2013 | Kiani et al. |
| 8,399,822 B2 | 3/2013 | Al-Ali |
| 8,401,602 B2 | 3/2013 | Kiani |
| 8,401,874 B2 | 3/2013 | Rosenfeld |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,704 B2 | 6/2013 | Sweitzer et al. |
| 8,457,707 B2 | 6/2013 | Kiani |
| 8,463,349 B2 | 6/2013 | Diab et al. |
| 8,466,286 B2 | 6/2013 | Bellot et al. |
| 8,467,556 B2 | 6/2013 | Shennib et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,167 B2 | 7/2013 | Buxton et al. |
| 8,489,364 B2 | 7/2013 | Weber et al. |
| 8,498,684 B2 | 7/2013 | Weber et al. |
| 8,500,692 B2 | 8/2013 | Yodfat et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,545,445 B2 | 10/2013 | Kamen et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,564,613 B2 | 10/2013 | Prior et al. |
| 8,565,847 B2 | 10/2013 | Buxton et al. |
| 8,568,361 B2 | 10/2013 | Yodfat et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,578,082 B2 | 11/2013 | Medina et al. |
| 8,579,813 B2 | 11/2013 | Causey, III et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,588,924 B2 | 11/2013 | Dion |
| 8,597,287 B2 | 12/2013 | Benamou et al. |
| 8,600,467 B2 | 12/2013 | Al-Ali et al. |
| 8,600,777 B2 | 12/2013 | Schoenberg |
| 8,606,342 B2 | 12/2013 | Diab |
| 8,615,281 B2 | 12/2013 | Yodfat et al. |
| 8,620,678 B2 | 12/2013 | Gotlib |
| 8,626,255 B2 | 1/2014 | Al-Ali et al. |
| 8,630,691 B2 | 1/2014 | Lamego et al. |

(56) References Cited

U.S. PATENT DOCUMENTS

| | | |
|---|---|---|
| 8,634,889 B2 | 1/2014 | Al-Ali et al. |
| 8,641,631 B2 | 2/2014 | Sierra et al. |
| 8,641,670 B2 | 2/2014 | Yodfat et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,810 B2 | 3/2014 | Isaacson |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,690,771 B2 | 4/2014 | Wekell et al. |
| 8,690,799 B2 | 4/2014 | Telfort et al. |
| 8,695,206 B2 | 4/2014 | Isaacson et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,725,226 B2 | 5/2014 | Isaacson et al. |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,761,852 B2 | 6/2014 | Parthasarathy |
| D709,846 S | 7/2014 | Oswaks |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,792,950 B2 | 7/2014 | Larsen et al. |
| 8,801,613 B2 | 8/2014 | Al-Ali et al. |
| 8,814,822 B2 | 8/2014 | Yodfat et al. |
| 8,818,477 B2 | 8/2014 | Soller |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,845,530 B2 | 9/2014 | Bruce et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,866,620 B2 | 10/2014 | Amir |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,873,035 B2 | 10/2014 | Yang et al. |
| D718,455 S | 11/2014 | Maser et al. |
| 8,878,888 B2 | 11/2014 | Rosenfeld |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,903,467 B2 | 12/2014 | Sweitzer et al. |
| 8,907,287 B2 | 12/2014 | Vanderpohl |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,939,914 B2 | 1/2015 | Turnquist et al. |
| 8,942,777 B2 | 1/2015 | Diab et al. |
| 8,948,834 B2 | 2/2015 | Diab et al. |
| 8,948,835 B2 | 2/2015 | Diab |
| 8,951,248 B2 | 2/2015 | Messerly et al. |
| 8,956,292 B2 | 2/2015 | Wekell et al. |
| 8,962,170 B2 | 2/2015 | Frey et al. |
| 8,965,471 B2 | 2/2015 | Lamego |
| 8,977,351 B2 | 3/2015 | Kivisto |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,014,778 B2 | 4/2015 | Datta et al. |
| 9,017,355 B2 | 4/2015 | Smith et al. |
| 9,028,407 B1 | 5/2015 | Bennett-Guerrero |
| 9,028,429 B2 | 5/2015 | Telfort et al. |
| 9,037,207 B2 | 5/2015 | Al-Ali et al. |
| 9,041,529 B2 | 5/2015 | Booij et al. |
| 9,057,689 B2 | 6/2015 | Soller |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,291 B2 | 8/2015 | Soller |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,149,228 B2 | 10/2015 | Kinast |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,173,993 B2 | 11/2015 | Yodfat et al. |
| 9,176,141 B2 | 11/2015 | Al-Ali et al. |
| 9,183,738 B1 | 11/2015 | Allen, Sr. et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| D745,167 S | 12/2015 | Canas et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,254,087 B2 | 2/2016 | Isaacson et al. |
| 9,259,185 B2 | 2/2016 | Abdul-Hafiz et al. |
| 9,262,586 B2 | 2/2016 | Steiger et al. |
| 9,267,572 B2 | 2/2016 | Barker et al. |
| 9,277,864 B2 | 3/2016 | Yang et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |

(56) References Cited

U.S. PATENT DOCUMENTS

| | | |
|---|---|---|
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,155 B2 | 6/2016 | Bardy et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-ali et al. |
| 9,375,179 B2 | 6/2016 | Schultz et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,402,544 B2 | 8/2016 | Yee et al. |
| 9,436,645 B2 | 9/2016 | Al-Ali et al. |
| 9,439,566 B2 | 9/2016 | Arne et al. |
| 9,480,408 B2 | 11/2016 | Isaacson et al. |
| 9,498,158 B2 | 11/2016 | Isaacson |
| 9,529,762 B2 | 12/2016 | Gisler et al. |
| 2001/0011355 A1 | 8/2001 | Kawai |
| 2001/0031922 A1 | 10/2001 | Weng et al. |
| 2001/0046366 A1 | 11/2001 | Susskind |
| 2002/0045836 A1 | 4/2002 | Alkawwas |
| 2002/0052311 A1 | 5/2002 | Solomon et al. |
| 2002/0063690 A1 | 5/2002 | Chung et al. |
| 2002/0099277 A1 | 7/2002 | Harry et al. |
| 2002/0107436 A1 | 8/2002 | Barton |
| 2002/0140675 A1 | 10/2002 | Ali et al. |
| 2002/0165462 A1 | 11/2002 | Westbrook et al. |
| 2002/0177758 A1 | 11/2002 | Schoenberg |
| 2002/0198445 A1 | 12/2002 | Dominguez et al. |
| 2003/0027326 A1 | 2/2003 | Ulmsten et al. |
| 2003/0033102 A1 | 2/2003 | Dietiker |
| 2003/0052787 A1 | 3/2003 | Zerhusen et al. |
| 2003/0058838 A1 | 3/2003 | Wengrovitz |
| 2003/0149349 A1 | 8/2003 | Jensen |
| 2003/0158466 A1 | 8/2003 | Lynn et al. |
| 2003/0181798 A1 | 9/2003 | Al-Ali |
| 2003/0181817 A1 | 9/2003 | Mori |
| 2003/0214408 A1 | 11/2003 | Grajales et al. |
| 2003/0216670 A1 | 11/2003 | Beggs |
| 2003/0229276 A1 | 12/2003 | Sarussi et al. |
| 2004/0000713 A1 | 1/2004 | Yamashita et al. |
| 2004/0013647 A1 | 1/2004 | Solomon et al. |
| 2004/0097797 A1 | 5/2004 | Porges |
| 2004/0102687 A1 | 5/2004 | Brashears et al. |
| 2004/0122787 A1 | 6/2004 | Avinash et al. |
| 2004/0126007 A1 | 7/2004 | Ziel et al. |
| 2004/0127775 A1 | 7/2004 | Miyazaki et al. |
| 2004/0139571 A1 | 7/2004 | Chang et al. |
| 2004/0147818 A1 | 7/2004 | Levy et al. |
| 2004/0186357 A1 | 9/2004 | Soderberg et al. |
| 2004/0230118 A1 | 11/2004 | Shehada et al. |
| 2004/0230132 A1 | 11/2004 | Shehada et al. |
| 2004/0230179 A1 | 11/2004 | Shehada et al. |
| 2004/0242976 A1 | 12/2004 | Abreu |
| 2004/0243017 A1 | 12/2004 | Causevic |
| 2004/0249670 A1 | 12/2004 | Noguchi et al. |
| 2004/0254431 A1 | 12/2004 | Shehada et al. |
| 2004/0254432 A1 | 12/2004 | Shehada et al. |
| 2004/0260161 A1 | 12/2004 | Melker et al. |
| 2004/0267103 A1 | 12/2004 | Li et al. |
| 2005/0010087 A1 | 1/2005 | Banet et al. |
| 2005/0020918 A1 | 1/2005 | Wilk et al. |
| 2005/0038326 A1 | 2/2005 | Mathur |
| 2005/0038332 A1 | 2/2005 | Saidara et al. |
| 2005/0038680 A1 | 2/2005 | McMahon |
| 2005/0070773 A1 | 3/2005 | Chin et al. |
| 2005/0070775 A1 | 3/2005 | Chin et al. |
| 2005/0080336 A1 | 4/2005 | Byrd et al. |
| 2005/0096542 A1 | 5/2005 | Weng et al. |
| 2005/0106713 A1 | 5/2005 | Phan et al. |
| 2005/0113653 A1 | 5/2005 | Fox et al. |
| 2005/0113655 A1 | 5/2005 | Hull |
| 2005/0119580 A1 | 6/2005 | Eveland |
| 2005/0124864 A1 | 6/2005 | Mack et al. |
| 2005/0125256 A1 | 6/2005 | Schoenberg |
| 2005/0131288 A1 | 6/2005 | Turner et al. |
| 2005/0164933 A1 | 7/2005 | Tymianski et al. |
| 2005/0191294 A1 | 9/2005 | Arap et al. |
| 2005/0197550 A1 | 9/2005 | Al-Ali et al. |
| 2005/0228298 A1 | 10/2005 | Banet et al. |
| 2005/0228299 A1 | 10/2005 | Banet |
| 2005/0234317 A1 | 10/2005 | Kiani |
| 2005/0245839 A1 | 11/2005 | Stivoric |
| 2005/0268401 A1 | 12/2005 | Dixon et al. |
| 2005/0277872 A1 | 12/2005 | Colby, Jr. et al. |
| 2006/0049936 A1 | 3/2006 | Collins, Jr. et al. |
| 2006/0058647 A1 | 3/2006 | Strommer et al. |
| 2006/0089543 A1 | 4/2006 | Kim et al. |
| 2006/0089546 A1 | 4/2006 | Mahony et al. |
| 2006/0094936 A1 | 5/2006 | Russ |
| 2006/0106294 A1 | 5/2006 | Maser et al. |
| 2006/0149393 A1 | 7/2006 | Calderon |
| 2006/0155175 A1 | 7/2006 | Ogino et al. |
| 2006/0167351 A1 | 7/2006 | Isaacson et al. |
| 2006/0217684 A1 | 9/2006 | Shehada et al. |
| 2006/0217685 A1 | 9/2006 | Shehada et al. |
| 2006/0224413 A1 | 10/2006 | Kim et al. |
| 2006/0235300 A1 | 10/2006 | Weng et al. |
| 2006/0253042 A1 | 11/2006 | Stahmann et al. |
| 2006/0276714 A1 | 12/2006 | Holt et al. |
| 2007/0000490 A1 | 1/2007 | DeVries et al. |
| 2007/0002533 A1 | 1/2007 | Kogan et al. |
| 2007/0021675 A1 | 1/2007 | Childre et al. |
| 2007/0027368 A1 | 2/2007 | Collins et al. |
| 2007/0032733 A1 | 2/2007 | Burton et al. |
| 2007/0055116 A1 | 3/2007 | Clark et al. |
| 2007/0055544 A1 | 3/2007 | Jung et al. |
| 2007/0060798 A1 | 3/2007 | Krupnik et al. |
| 2007/0088406 A1 | 4/2007 | Bennett et al. |
| 2007/0096897 A1 | 5/2007 | Weiner |
| 2007/0100222 A1 | 5/2007 | Mastrototaro et al. |
| 2007/0118399 A1 | 5/2007 | Avinash et al. |
| 2007/0140475 A1 | 6/2007 | Kurtock et al. |
| 2007/0156033 A1 | 7/2007 | Causey et al. |
| 2007/0157285 A1 | 7/2007 | Frank et al. |
| 2007/0159332 A1 | 7/2007 | Koblasz |
| 2007/0163589 A1 | 7/2007 | DeVries et al. |
| 2007/0185390 A1 | 8/2007 | Perkins et al. |
| 2007/0232941 A1 | 10/2007 | Rabinovich |
| 2007/0244724 A1 | 10/2007 | Pendergast et al. |
| 2007/0254593 A1 | 11/2007 | Jollota et al. |
| 2007/0255114 A1 | 11/2007 | Ackermann et al. |
| 2007/0255116 A1 | 11/2007 | Mehta et al. |
| 2007/0255250 A1 | 11/2007 | Moberg |
| 2007/0282478 A1 | 12/2007 | Al-Ali et al. |
| 2008/0000479 A1 | 1/2008 | Elaz et al. |
| 2008/0003200 A1 | 1/2008 | Arap et al. |
| 2008/0021854 A1 | 1/2008 | Jung et al. |
| 2008/0033661 A1 | 2/2008 | Syroid et al. |
| 2008/0039701 A1 | 2/2008 | Ali et al. |
| 2008/0053438 A1 | 3/2008 | DeVries et al. |
| 2008/0058657 A1 | 3/2008 | Schwartz et al. |
| 2008/0090626 A1 | 4/2008 | Griffin et al. |
| 2008/0091089 A1 | 4/2008 | Guillory et al. |
| 2008/0091090 A1 | 4/2008 | Guillory et al. |
| 2008/0091471 A1 | 4/2008 | Michon et al. |
| 2008/0097167 A1 | 4/2008 | Yudkovitch et al. |
| 2008/0099366 A1 | 5/2008 | Niemiec et al. |
| 2008/0113621 A1 | 5/2008 | Parthasarathy |
| 2008/0119412 A1 | 5/2008 | Tymianski et al. |
| 2008/0138278 A1 | 6/2008 | Scherz et al. |
| 2008/0169922 A1 | 7/2008 | Issokson |
| 2008/0171919 A1 | 7/2008 | Stivoric et al. |
| 2008/0188795 A1 | 8/2008 | Katz et al. |
| 2008/0194918 A1 | 8/2008 | Kulik et al. |

(56) References Cited

U.S. PATENT DOCUMENTS

| | | |
|---|---|---|
| 2008/0208009 A1 | 8/2008 | Shklarski |
| 2008/0208023 A1 | 8/2008 | Grubac et al. |
| 2008/0208912 A1 | 8/2008 | Garibaldi |
| 2008/0221396 A1 | 9/2008 | Garces et al. |
| 2008/0221420 A1 | 9/2008 | Grubac et al. |
| 2008/0222251 A1 | 9/2008 | Parthasarathy |
| 2008/0228077 A1 | 9/2008 | Wilk et al. |
| 2008/0275309 A1 | 11/2008 | Stivoric et al. |
| 2008/0281167 A1 | 11/2008 | Soderberg et al. |
| 2008/0281168 A1 | 11/2008 | Gibson et al. |
| 2008/0281181 A1 | 11/2008 | Manzione et al. |
| 2008/0287751 A1 | 11/2008 | Stivoric et al. |
| 2008/0292172 A1 | 11/2008 | Assmann et al. |
| 2008/0300020 A1 | 12/2008 | Nishizawa et al. |
| 2008/0319275 A1 | 12/2008 | Chiu et al. |
| 2008/0319354 A1 | 12/2008 | Bell et al. |
| 2009/0005651 A1 | 1/2009 | Ward et al. |
| 2009/0018808 A1 | 1/2009 | Bronstein et al. |
| 2009/0024008 A1 | 1/2009 | Brunner et al. |
| 2009/0043172 A1 | 2/2009 | Zagorchev et al. |
| 2009/0043180 A1 | 2/2009 | Tschautscher et al. |
| 2009/0052623 A1 | 2/2009 | Tome et al. |
| 2009/0054735 A1 | 2/2009 | Higgins et al. |
| 2009/0062682 A1 | 3/2009 | Bland et al. |
| 2009/0069642 A1 | 3/2009 | Gao et al. |
| 2009/0099480 A1 | 4/2009 | Salgo et al. |
| 2009/0119330 A1 | 5/2009 | Sampath et al. |
| 2009/0119843 A1 | 5/2009 | Rodgers et al. |
| 2009/0124867 A1 | 5/2009 | Hirsch et al. |
| 2009/0131759 A1 | 5/2009 | Sims et al. |
| 2009/0143832 A1 | 6/2009 | Saba |
| 2009/0157058 A1 | 6/2009 | Ferren et al. |
| 2009/0171170 A1 | 7/2009 | Li et al. |
| 2009/0171225 A1 | 7/2009 | Gadodia et al. |
| 2009/0177090 A1 | 7/2009 | Grunwald et al. |
| 2009/0182287 A1 | 7/2009 | Kassab |
| 2009/0226372 A1 | 9/2009 | Ruoslahti et al. |
| 2009/0247984 A1 | 10/2009 | Lamego et al. |
| 2009/0259114 A1 | 10/2009 | Johnson et al. |
| 2009/0264778 A1 | 10/2009 | Markowitz et al. |
| 2009/0275813 A1 | 11/2009 | Davis |
| 2009/0275844 A1 | 11/2009 | Al-Ali |
| 2009/0281462 A1 | 11/2009 | Heliot et al. |
| 2009/0299157 A1 | 12/2009 | Telfort et al. |
| 2009/0299675 A1 | 12/2009 | Isaacson et al. |
| 2009/0309645 A1 | 12/2009 | Isaacson et al. |
| 2009/0309755 A1 | 12/2009 | Williamson et al. |
| 2009/0322540 A1 | 12/2009 | Richardson et al. |
| 2010/0004518 A1 | 1/2010 | Vo et al. |
| 2010/0030040 A1 | 2/2010 | Poeze et al. |
| 2010/0030094 A1 | 2/2010 | Lundback |
| 2010/0036209 A1 | 2/2010 | Ferren et al. |
| 2010/0069725 A1 | 3/2010 | Al-Ali |
| 2010/0125188 A1 | 5/2010 | Schilling et al. |
| 2010/0125217 A1 | 5/2010 | Kuo et al. |
| 2010/0130840 A1 | 5/2010 | Isaacson et al. |
| 2010/0144627 A1 | 6/2010 | Vitek et al. |
| 2010/0185101 A1 | 7/2010 | Sakai et al. |
| 2010/0198622 A1 | 8/2010 | Gajic et al. |
| 2010/0210924 A1 | 8/2010 | Parthasarathy |
| 2010/0210958 A1 | 8/2010 | Manwaring et al. |
| 2010/0298659 A1 | 11/2010 | McCombie et al. |
| 2010/0298660 A1 | 11/2010 | McCombie et al. |
| 2010/0298661 A1 | 11/2010 | McCombie et al. |
| 2010/0298742 A1 | 11/2010 | Perlman et al. |
| 2010/0305412 A1 | 12/2010 | Darrah et al. |
| 2010/0309207 A1 | 12/2010 | Prior et al. |
| 2010/0312079 A1 | 12/2010 | Larsen et al. |
| 2010/0312080 A1 | 12/2010 | Isaacson |
| 2010/0312103 A1 | 12/2010 | Gorek et al. |
| 2010/0317936 A1 | 12/2010 | Al-Ali et al. |
| 2010/0317951 A1 | 12/2010 | Rutkowski et al. |
| 2011/0021930 A1 | 1/2011 | Mazzeo et al. |
| 2011/0023130 A1 | 1/2011 | Gudgel et al. |
| 2011/0028809 A1 | 2/2011 | Goodman |
| 2011/0046495 A1 | 2/2011 | Osypka |
| 2011/0066051 A1 | 3/2011 | Moon et al. |
| 2011/0077473 A1 | 3/2011 | Lisogurski |
| 2011/0078596 A1 | 3/2011 | Rawlins et al. |
| 2011/0080294 A1 | 4/2011 | Tanishima et al. |
| 2011/0082711 A1 | 4/2011 | Poeze et al. |
| 2011/0087083 A1 | 4/2011 | Poeze et al. |
| 2011/0087084 A1 | 4/2011 | Jeong et al. |
| 2011/0087117 A1 | 4/2011 | Tremper et al. |
| 2011/0087756 A1 | 4/2011 | Biondi |
| 2011/0098583 A1 | 4/2011 | Pandia et al. |
| 2011/0105854 A1 | 5/2011 | Kiani et al. |
| 2011/0105956 A1 | 5/2011 | Hirth |
| 2011/0118573 A1 | 5/2011 | Mckenna |
| 2011/0125060 A1 | 5/2011 | Telfort et al. |
| 2011/0152629 A1 | 6/2011 | Eaton et al. |
| 2011/0172967 A1 | 7/2011 | Al-Ali et al. |
| 2011/0184252 A1 | 7/2011 | Archer et al. |
| 2011/0184253 A1 | 7/2011 | Archer et al. |
| 2011/0208015 A1 | 8/2011 | Welch et al. |
| 2011/0208018 A1 | 8/2011 | Kiani |
| 2011/0208073 A1 | 8/2011 | Matsukawa et al. |
| 2011/0209915 A1 | 9/2011 | Telfort et al. |
| 2011/0212090 A1 | 9/2011 | Pedersen et al. |
| 2011/0213212 A1 | 9/2011 | Al-Ali |
| 2011/0227739 A1 | 9/2011 | Gilham et al. |
| 2011/0230733 A1 | 9/2011 | Al-Ali |
| 2011/0237911 A1 | 9/2011 | Lamego et al. |
| 2011/0237969 A1 | 9/2011 | Eckerbom et al. |
| 2011/0257544 A1 | 10/2011 | Kaasinen et al. |
| 2011/0263203 A1 | 10/2011 | Parthasarathy |
| 2011/0288383 A1 | 11/2011 | Diab |
| 2011/0295094 A1 | 12/2011 | Doyle et al. |
| 2011/0301444 A1 | 12/2011 | Al-Ali |
| 2012/0004579 A1 | 1/2012 | Luo et al. |
| 2012/0029300 A1 | 2/2012 | Paquet |
| 2012/0029879 A1 | 2/2012 | Sing et al. |
| 2012/0041316 A1 | 2/2012 | Al-Ali et al. |
| 2012/0046557 A1 | 2/2012 | Kiani |
| 2012/0059230 A1 | 3/2012 | Teller et al. |
| 2012/0059267 A1 | 3/2012 | Lamego et al. |
| 2012/0071771 A1 | 3/2012 | Behar |
| 2012/0075464 A1 | 3/2012 | Derenne et al. |
| 2012/0088984 A1 | 4/2012 | Al-Ali et al. |
| 2012/0095778 A1 | 4/2012 | Gross et al. |
| 2012/0101353 A1 | 4/2012 | Reggiardo et al. |
| 2012/0116175 A1 | 5/2012 | Al-Ali et al. |
| 2012/0123799 A1 | 5/2012 | Nolen et al. |
| 2012/0136221 A1 | 5/2012 | Killen et al. |
| 2012/0165629 A1 | 6/2012 | Merritt et al. |
| 2012/0179006 A1 | 7/2012 | Jansen et al. |
| 2012/0184120 A1 | 7/2012 | Basta et al. |
| 2012/0197619 A1 | 8/2012 | Namer Yelin et al. |
| 2012/0203078 A1 | 8/2012 | Sze et al. |
| 2012/0209082 A1 | 8/2012 | Al-Ali |
| 2012/0209084 A1 | 8/2012 | Olsen et al. |
| 2012/0226160 A1 | 9/2012 | Kudoh |
| 2012/0227739 A1 | 9/2012 | Kiani |
| 2012/0239434 A1 | 9/2012 | Breslow et al. |
| 2012/0242501 A1 | 9/2012 | Tran et al. |
| 2012/0265039 A1 | 10/2012 | Kiani |
| 2012/0277597 A1 | 11/2012 | Eshbaugh et al. |
| 2012/0282583 A1 | 11/2012 | Thaler et al. |
| 2012/0283524 A1 | 11/2012 | Kiani et al. |
| 2012/0284053 A1 | 11/2012 | Rosenfeld |
| 2012/0286955 A1 | 11/2012 | Welch et al. |
| 2012/0289800 A1 | 11/2012 | Isaacson et al. |
| 2012/0294801 A1 | 11/2012 | Scherz et al. |
| 2012/0296178 A1 | 11/2012 | Lamego et al. |
| 2012/0302894 A1 | 11/2012 | Diab et al. |
| 2012/0303476 A1 | 11/2012 | Krzyzanowski et al. |
| 2012/0304784 A1 | 12/2012 | Isaacson et al. |
| 2012/0319816 A1 | 12/2012 | Al-Ali |
| 2012/0330112 A1 | 12/2012 | Lamego et al. |
| 2013/0006131 A1 | 1/2013 | Narayan et al. |
| 2013/0006151 A1 | 1/2013 | Main et al. |
| 2013/0023775 A1 | 1/2013 | Lamego et al. |
| 2013/0035603 A1 | 2/2013 | Jarausch et al. |
| 2013/0041591 A1 | 2/2013 | Lamego |

(56) References Cited

U.S. PATENT DOCUMENTS

| | | |
|---|---|---|
| 2013/0046197 A1 | 2/2013 | Dlugos, Jr. et al. |
| 2013/0046204 A1 | 2/2013 | Lamego et al. |
| 2013/0060108 A1 | 3/2013 | Schurman et al. |
| 2013/0060147 A1 | 3/2013 | Welch et al. |
| 2013/0079610 A1 | 3/2013 | Al-Ali |
| 2013/0092805 A1 | 4/2013 | Funk et al. |
| 2013/0096405 A1 | 4/2013 | Garfio |
| 2013/0096936 A1 | 4/2013 | Sampath et al. |
| 2013/0109929 A1 | 5/2013 | Menzel |
| 2013/0109935 A1 | 5/2013 | Al-Ali et al. |
| 2013/0123616 A1 | 5/2013 | Merritt et al. |
| 2013/0162433 A1 | 6/2013 | Muhsin et al. |
| 2013/0178749 A1 | 7/2013 | Lamego |
| 2013/0190581 A1 | 7/2013 | Al-Ali et al. |
| 2013/0197328 A1 | 8/2013 | Diab et al. |
| 2013/0197364 A1 | 8/2013 | Han |
| 2013/0211214 A1 | 8/2013 | Olsen |
| 2013/0243021 A1 | 9/2013 | Siskavich |
| 2013/0253334 A1 | 9/2013 | Al-Ali et al. |
| 2013/0261494 A1 | 10/2013 | Bloom et al. |
| 2013/0267804 A1 | 10/2013 | Al-Ali |
| 2013/0274571 A1 | 10/2013 | Diab et al. |
| 2013/0274572 A1 | 10/2013 | Al-Ali et al. |
| 2013/0279109 A1 | 10/2013 | Lindblad et al. |
| 2013/0296672 A1 | 11/2013 | O'Neil et al. |
| 2013/0296713 A1 | 11/2013 | Al-Ali et al. |
| 2013/0310667 A1 | 11/2013 | Grubac et al. |
| 2013/0317327 A1 | 11/2013 | Al-Ali et al. |
| 2013/0317370 A1 | 11/2013 | Dalvi et al. |
| 2013/0317393 A1 | 11/2013 | Weiss et al. |
| 2013/0324804 A1 | 12/2013 | McKeown et al. |
| 2013/0324808 A1 | 12/2013 | Al-Ali et al. |
| 2013/0324817 A1 | 12/2013 | Diab |
| 2013/0331660 A1 | 12/2013 | Al-Ali et al. |
| 2013/0331670 A1 | 12/2013 | Kiani |
| 2013/0338461 A1 | 12/2013 | Lamego et al. |
| 2013/0340176 A1 | 12/2013 | Stevens et al. |
| 2014/0012100 A1 | 1/2014 | Al-Ali et al. |
| 2014/0022081 A1 | 1/2014 | Ribble et al. |
| 2014/0025306 A1 | 1/2014 | Weber et al. |
| 2014/0031650 A1 | 1/2014 | Weber et al. |
| 2014/0034353 A1 | 2/2014 | Al-Ali et al. |
| 2014/0046674 A1 | 2/2014 | Rosenfeld |
| 2014/0051952 A1 | 2/2014 | Reichgott et al. |
| 2014/0051953 A1 | 2/2014 | Lamego et al. |
| 2014/0051954 A1 | 2/2014 | Al-Ali et al. |
| 2014/0058230 A1 | 2/2014 | Abdul-Hafiz et al. |
| 2014/0066783 A1 | 3/2014 | Kiani et al. |
| 2014/0066880 A1 | 3/2014 | Prince et al. |
| 2014/0073167 A1 | 3/2014 | Al-Ali et al. |
| 2014/0077956 A1 | 3/2014 | Sampath et al. |
| 2014/0081097 A1 | 3/2014 | Al-Ali et al. |
| 2014/0081100 A1 | 3/2014 | Muhsin et al. |
| 2014/0081175 A1 | 3/2014 | Telfort |
| 2014/0094667 A1 | 4/2014 | Schurman et al. |
| 2014/0100434 A1 | 4/2014 | Diab et al. |
| 2014/0114199 A1 | 4/2014 | Lamego et al. |
| 2014/0120564 A1 | 5/2014 | Workman et al. |
| 2014/0121482 A1 | 5/2014 | Merritt et al. |
| 2014/0121483 A1 | 5/2014 | Kiani |
| 2014/0127137 A1 | 5/2014 | Bellott et al. |
| 2014/0128696 A1 | 5/2014 | Al-Ali |
| 2014/0128699 A1 | 5/2014 | Al-Ali et al. |
| 2014/0129702 A1 | 5/2014 | Lamego et al. |
| 2014/0135588 A1 | 5/2014 | Al-Ali et al. |
| 2014/0135602 A1 | 5/2014 | Lemke et al. |
| 2014/0142399 A1 | 5/2014 | Al-Ali et al. |
| 2014/0142401 A1 | 5/2014 | Al-Ali et al. |
| 2014/0142402 A1 | 5/2014 | Al-Ali et al. |
| 2014/0152673 A1 | 6/2014 | Lynn et al. |
| 2014/0155712 A1 | 6/2014 | Lamego et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0188516 A1 | 7/2014 | Kamen |
| 2014/0194709 A1 | 7/2014 | Al-Ali et al. |
| 2014/0194711 A1 | 7/2014 | Al-Ali |
| 2014/0194766 A1 | 7/2014 | Al-Ali et al. |
| 2014/0200422 A1 | 7/2014 | Weber et al. |
| 2014/0206963 A1 | 7/2014 | Al-Ali |
| 2014/0213864 A1 | 7/2014 | Abdul-Hafiz et al. |
| 2014/0221798 A1 | 8/2014 | Isaacson |
| 2014/0243627 A1 | 8/2014 | Diab et al. |
| 2014/0243632 A1 | 8/2014 | Ulrich et al. |
| 2014/0257057 A1 | 9/2014 | Reis Cunha et al. |
| 2014/0266787 A1 | 9/2014 | Tran |
| 2014/0266790 A1 | 9/2014 | Al-Ali et al. |
| 2014/0275808 A1 | 9/2014 | Poeze et al. |
| 2014/0275816 A1 | 9/2014 | Sandmore |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0275881 A1 | 9/2014 | Lamego et al. |
| 2014/0275883 A1 | 9/2014 | Haisley et al. |
| 2014/0275885 A1 | 9/2014 | Isaacson et al. |
| 2014/0275932 A1 | 9/2014 | Zadig |
| 2014/0276115 A1 | 9/2014 | Dalvi et al. |
| 2014/0288388 A1 | 9/2014 | Isaacson et al. |
| 2014/0288400 A1 | 9/2014 | Diab et al. |
| 2014/0296664 A1 | 10/2014 | Bruinsma et al. |
| 2014/0303520 A1 | 10/2014 | Telfort et al. |
| 2014/0309506 A1 | 10/2014 | Lamego et al. |
| 2014/0309559 A1 | 10/2014 | Telfort et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0330099 A1 | 11/2014 | Al-Ali et al. |
| 2014/0333440 A1 | 11/2014 | Kiani |
| 2014/0336481 A1 | 11/2014 | Shakespeare et al. |
| 2014/0343389 A1 | 11/2014 | Goldstein et al. |
| 2014/0343436 A1 | 11/2014 | Kiani |
| 2014/0343889 A1 | 11/2014 | Ben Shalom et al. |
| 2014/0357966 A1 | 12/2014 | Al-Ali et al. |
| 2014/0357970 A1 | 12/2014 | Larsen et al. |
| 2014/0364705 A1 | 12/2014 | Parthasarathy et al. |
| 2014/0371548 A1 | 12/2014 | Al-Ali et al. |
| 2014/0371632 A1 | 12/2014 | Al-Ali et al. |
| 2014/0378784 A1 | 12/2014 | Kiani et al. |
| 2015/0005600 A1 | 1/2015 | Blank et al. |
| 2015/0011907 A1 | 1/2015 | Purdon et al. |
| 2015/0012231 A1 | 1/2015 | Poeze et al. |
| 2015/0018650 A1 | 1/2015 | Al-Ali et al. |
| 2015/0025406 A1 | 1/2015 | Al-Ali |
| 2015/0031970 A1 | 1/2015 | Lain |
| 2015/0032029 A1 | 1/2015 | Al-Ali et al. |
| 2015/0038859 A1 | 2/2015 | Dalvi et al. |
| 2015/0045637 A1 | 2/2015 | Dalvi |
| 2015/0051462 A1 | 2/2015 | Olsen |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0094618 A1 | 4/2015 | Russell et al. |
| 2015/0097701 A1 | 4/2015 | Al-Ali et al. |
| 2015/0099950 A1 | 4/2015 | Al-Ali et al. |
| 2015/0099951 A1 | 4/2015 | Al-Ali et al. |
| 2015/0099955 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0116076 A1 | 4/2015 | Al-Ali et al. |
| 2015/0126830 A1 | 5/2015 | Schurman et al. |
| 2015/0133755 A1 | 5/2015 | Smith et al. |
| 2015/0140863 A1 | 5/2015 | Al-Ali et al. |
| 2015/0141779 A1 | 5/2015 | Johnson et al. |

(56) References Cited

U.S. PATENT DOCUMENTS

| | | |
|---|---|---|
| 2015/0141780 A1 | 5/2015 | Meyer et al. |
| 2015/0141781 A1 | 5/2015 | Weber et al. |
| 2015/0165312 A1 | 6/2015 | Kiani |
| 2015/0196237 A1 | 7/2015 | Lamego |
| 2015/0201874 A1 | 7/2015 | Diab |
| 2015/0208966 A1 | 7/2015 | Al-Ali |
| 2015/0216459 A1 | 8/2015 | Al-Ali et al. |
| 2015/0230755 A1 | 8/2015 | Al-Ali et al. |
| 2015/0238094 A1 | 8/2015 | Lai et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0272514 A1 | 10/2015 | Kiani et al. |
| 2015/0289814 A1 | 10/2015 | Magar et al. |
| 2015/0351697 A1 | 12/2015 | Weber et al. |
| 2015/0351704 A1 | 12/2015 | Kiani et al. |
| 2015/0359429 A1 | 12/2015 | Al-Ali et al. |
| 2015/0366472 A1 | 12/2015 | Kiani |
| 2015/0366507 A1 | 12/2015 | Blank |
| 2015/0374298 A1 | 12/2015 | Al-Ali et al. |
| 2015/0374905 A1 | 12/2015 | Yodfat et al. |
| 2015/0380875 A1 | 12/2015 | Coverston et al. |
| 2016/0000362 A1 | 1/2016 | Diab et al. |
| 2016/0007930 A1 | 1/2016 | Weber et al. |
| 2016/0029932 A1 | 2/2016 | Al-Ali |
| 2016/0029933 A1 | 2/2016 | Al-Ali et al. |
| 2016/0045118 A1 | 2/2016 | Kiani |
| 2016/0051205 A1 | 2/2016 | Al-Ali et al. |
| 2016/0058338 A1 | 3/2016 | Schurman et al. |
| 2016/0058347 A1 | 3/2016 | Reichgott et al. |
| 2016/0066823 A1 | 3/2016 | Al-Ali et al. |
| 2016/0066824 A1 | 3/2016 | Al-Ali et al. |
| 2016/0066879 A1 | 3/2016 | Telfort et al. |
| 2016/0072429 A1 | 3/2016 | Kiani et al. |
| 2016/0073967 A1 | 3/2016 | Lamego et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0106914 A1 | 4/2016 | Yodfat et al. |
| 2016/0113527 A1 | 4/2016 | Al-Ali |
| 2016/0143548 A1 | 5/2016 | Al-Ali |
| 2016/0166183 A1 | 6/2016 | Poeze et al. |
| 2016/0166188 A1 | 6/2016 | Bruinsma et al. |
| 2016/0166210 A1 | 6/2016 | Al-Ali |
| 2016/0166213 A1 | 6/2016 | Isaacson |
| 2016/0192869 A1 | 7/2016 | Kiani et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0235344 A1 | 8/2016 | Auerbach |
| 2016/0262673 A1 | 9/2016 | Skorich et al. |
| 2016/0324486 A1 | 11/2016 | Al-Ali et al. |
| 2016/0327984 A1 | 11/2016 | Al-Ali et al. |
| 2016/0328528 A1 | 11/2016 | Al-Ali et al. |
| 2016/0359150 A1 | 12/2016 | Martin et al. |
| 2016/0367164 A1 | 12/2016 | Felix |

FOREIGN PATENT DOCUMENTS

| | | |
|---|---|---|
| EP | 1408823 | 5/2010 |
| EP | 2 335 569 | 6/2011 |
| EP | 2 766 834 | 8/2014 |
| EP | 2 811 894 | 12/2014 |
| JP | 10-336064 | 12/1998 |
| JP | 2001-501847 | 2/2001 |
| JP | 2002-165764 | 6/2002 |
| JP | 2002-172096 | 6/2002 |
| JP | 2003-275183 | 9/2003 |
| JP | 2004-024551 | 1/2004 |
| JP | 2005-218036 | 8/2005 |
| JP | 2005-295375 | 10/2005 |
| JP | 2007-021213 | 2/2007 |
| JP | 2007-095365 | 4/2007 |
| JP | 2007-174051 | 7/2007 |
| JP | 2008-541045 | 11/2008 |
| JP | 2009-017959 | 1/2009 |
| JP | 2009-207836 | 9/2009 |
| JP | 2010-503134 | 1/2010 |
| JP | 2010-524510 | 7/2010 |
| JP | 2011-519607 | 7/2011 |
| JP | 2011-152261 | 8/2011 |
| JP | 2014-533997 | 12/2014 |
| RU | 2199723 | 2/2003 |
| WO | WO 1996/016591 | 6/1996 |
| WO | WO 1997/000708 | 1/1997 |
| WO | WO 1998/015224 | 4/1998 |
| WO | WO 98/029790 | 7/1998 |
| WO | WO 1998/039749 | 9/1998 |
| WO | WO 99/013766 | 3/1999 |
| WO | WO 99/056613 | 11/1999 |
| WO | WO 00/063713 | 10/2000 |
| WO | WO 2000/062665 | 10/2000 |
| WO | WO 2000/069328 | 11/2000 |
| WO | WO 2001/041634 | 6/2001 |
| WO | WO 2003/065926 | 8/2003 |
| WO | WO 2004/056266 | 7/2004 |
| WO | WO 2004/059551 | 7/2004 |
| WO | WO 2005/048830 | 6/2005 |
| WO | WO 2005/092177 | 10/2005 |
| WO | WO 2006/051461 | 5/2006 |
| WO | WO 2011/001302 | 1/2011 |
| WO | WO 2011/002904 | 1/2011 |
| WO | WO 2011/025549 | 3/2011 |
| WO | WO 2013/056160 | 4/2013 |
| WO | WO 2013/119982 | 8/2013 |
| WO | WO 2015/054665 | 4/2015 |

OTHER PUBLICATIONS

Capuano et al., "Remote Telemetry—New Twists for Old Technology", Nursing Management, Jul. 1995, vol. 26, No. 7, pp. 26-32.
Elmer-Dewitt, Philip, "Apple's iWatch: The killer apps may be in hospitals, not health clubs", Fortune.com, Feb. 3, 2014, http://fortune.com/2014/02/03/apples-iwatch-the-killer-apps-may-be-in-hospitals-not-health-clubs/, 4 pages.
Grundy et al., "Telemedicine in Critical Care: An Experiment in Health Care Delivery", JACEP, Oct. 1977, vol. 6, No. 10, pp. 439-444.
Grundy et al., "Telemedicine in Critical Care: Problems in Design, Implementation and Assessment", Jul. 1982, vol. 10, No. 7, pp. 471-475.
Rysavy, Peter, "Making the Call with Two-Way Paging", Network Computing, Published Jan. 15, 1997, www.rysavy.com/Articles/twoway.htm, pp. 5.
Wachter et al., "The Employment of an Iterative Design Process to Develop a Pulmonary Graphical Display", Journal of the American Medical Informatics Association, vol. 10, No. 4, Jul./Aug. 2003, pp. 363-372.
Official Communication in European Application No. 10195398.2 dated Jul. 5, 2012.
Official Communication in European Application No. 10195398.2 dated Jun. 15, 2015.
International Search Report & Written Opinion in PCT Application No. PCT/US2013/025384, dated Aug. 6, 2013.
International Search Report & Written Opinion in PCT Application No. PCT/US2012/060109, dated Jun. 5, 2013.
International Preliminary Report on Patentability in PCT Application No. PCT/US2012/060109, dated Apr. 24, 2014.
International Search Report & Written Opinion in PCT Application No. PCT/US2014/060177, dated Dec. 19, 2014.
International Preliminary Report on Patentability & Written Opinion in PCT Application No. PCT/US2013/025384, dated Aug. 21, 2014.
International Preliminary Report on Patentability & Written Opinion in PCT Application No. PCT/US2014/060177, dated Apr. 21, 2016.
Crilly et al., "An Integrated Pulse Oximeter System for Telemedicine Applications", IEEE Instrumentation and Measurement Technology Conference, Ottawa, Canada, May 19-21, 1997, in 3 pages.

(56) References Cited

OTHER PUBLICATIONS

"Medicine" Textbook of Anaesthesiology/Ed. By Aitkonhead A.R. et al., vol. 1, 1999, pp. 437-440.
Dissertation thesis for an MBA class given by the inventor on Dec. 18, 2004. "Reducing Health Care Costs and Improving Patient Care with the Uni-Ox Pulse Oximeter from Snap Medical Technologies", Robert Sweitzer and Samantha Goetz, in 7 pages.
European Search Report in EP Application No. 02 748 235.5, dated Oct. 4, 2006.
Official Communication in EP Application No. 02 748 235.5, dated Jul. 25, 2008.
International Search Report in PCT Application No. PCT/US02/03434, dated Dec. 19, 2002.

\* cited by examiner

WEARABLE PORTABLE PATIENT MONITOR

REFERENCE TO RELATED APPLICATION

The present application is a continuation of U.S. patent application Ser. No. 15/448,989, filed on Mar. 3, 2017, entitled "Physiological Measurement Communications Adapter," which is a continuation of U.S. patent application Ser. No. 14/815,232, filed on Jul. 31, 2015, entitled "Physiological Measurement Communications Adapter," which is a continuation of U.S. patent application Ser. No. 14/217,788, filed on Mar. 18, 2014, entitled "Wrist-Mounted Physiological Measurement Device," now U.S. Pat. No. 9,113,832, which is a continuation of U.S. patent application Ser. No. 14/037,137, filed on Sep. 25, 2013, entitled "Physiological Measurement Communications Adapter," now U.S. Pat. No. 9,113,831, which is a continuation of U.S. patent application Ser. No. 12/955,826, filed on Nov. 29, 2010, entitled "Physiological Measurement Communications Adapter," now U.S. Pat. No. 8,548,548, which is a continuation of U.S. patent application Ser. No. 11/417,006, filed on May 3, 2006, entitled "Physiological Measurement Communications Adapter," now U.S. Pat. No. 7,844,315, which claims priority benefit under 35 U.S.C. §120 to, and is a continuation of, U.S. patent application Ser. No. 11/048,330, filed Feb. 1, 2005, entitled "Physiological Measurement Communications Adapter," now U.S. Pat. No. 7,844,314, which is a continuation of U.S. patent application Ser. No. 10/377,933, entitled "Physiological Measurement Communications Adapter," now U.S. Pat. No. 6,850,788, which claims priority benefit under 35 U.S.C. §119(e) from U.S. Provisional Application No. 60/367,428, filed Mar. 25, 2002, entitled "Physiological Measurement Communications Adapter." The present application also incorporates the foregoing utility disclosures herein by reference.

BACKGROUND OF THE INVENTION

Patient vital sign monitoring may include measurements of blood oxygen, blood pressure, respiratory gas, and EKG among other parameters. Each of these physiological parameters typically requires a sensor in contact with a patient and a cable connecting the sensor to a monitoring device. For example, FIGS. 1-2 illustrate a conventional pulse oximetry system 100 used for the measurement of blood oxygen. As shown in FIG. 1, a pulse oximetry system has a sensor 110, a patient cable 140 and a monitor 160. The sensor 110 is typically attached to a finger 10 as shown. The sensor 110 has a plug 118 that inserts into a patient cable socket 142. The monitor 160 has a socket 162 that accepts a patient cable plug 144. The patient cable 140 transmits an LED drive signal 252 (FIG. 2) from the monitor 160 to the sensor 110 and a resulting detector signal 254 (FIG. 2) from the sensor 110 to the monitor 160. The monitor 160 processes the detector signal 254 (FIG. 2) to provide, typically, a numerical readout of the patient's oxygen saturation, a numerical readout of pulse rate, and an audible indicator or "beep" that occurs in response to each arterial pulse.

As shown in FIG. 2, the sensor 110 has both red and infrared LED emitters 212 and a photodiode detector 214. The monitor 160 has a sensor interface 271, a signal processor 273, a controller 275, output drivers 276, a display and audible indicator 278, and a keypad 279. The monitor 160 determines oxygen saturation by computing the differential absorption by arterial blood of the two wavelengths emitted by the sensor emitters 212, as is well-known in the art. The sensor interface 271 provides LED drive current 252 which alternately activates the red and IR LED emitters 212. The photodiode detector 214 generates a signal 254 corresponding to the red and infrared light energy attenuated from transmission through the patient finger 10 (FIG. 1). The sensor interface 271 also has input circuitry for amplification, filtering and digitization of the detector signal 254. The signal processor 273 calculates a ratio of detected red and infrared intensities, and an arterial oxygen saturation value is empirically determined based on that ratio. The controller 275 provides hardware and software interfaces for managing the display and audible indicator 278 and keypad 279. The display and audible indicator 278 shows the computed oxygen status, as described above, and provides the pulse beep as well as alarms indicating oxygen desaturation events. The keypad 279 provides a user interface for setting alarm thresholds, alarm enablement, and display options, to name a few.

SUMMARY OF THE INVENTION

Conventional physiological measurement systems are limited by the patient cable connection between sensor and monitor. A patient must be located in the immediate vicinity of the monitor. Also, patient relocation requires either disconnection of monitoring equipment and a corresponding loss of measurements or an awkward simultaneous movement of patient equipment and cables. Various devices have been proposed or implemented to provide wireless communication links between sensors and monitors, freeing patients from the patient cable tether. These devices, however, are incapable of working with the large installed base of existing monitors and sensors, requiring caregivers and medical institutions to suffer expensive wireless upgrades. It is desirable, therefore, to provide a communications adapter that is plug-compatible both with existing sensors and monitors and that implements a wireless link replacement for the patient cable.

An aspect of a physiological measurement communications adapter comprises a sensor interface configured to receive a sensor signal. A transmitter modulates a first baseband signal responsive to the sensor signal so as to generate a transmit signal. A receiver demodulates a receive signal corresponding to the transmit signal so as to generate a second baseband signal corresponding to the first baseband signal. Further, a monitor interface is configured to communicate a waveform responsive to the second baseband signal to a sensor port of a monitor. The waveform is adapted to the monitor so that measurements derived by the monitor from the waveform are generally equivalent to measurements derivable from the sensor signal. The communications adapter may further comprise a signal processor having an input in communications with the sensor interface, where the signal processor is operable to derive a parameter responsive to the sensor signal and where the first baseband signal is responsive to the parameter. The parameter may correspond to at least one of a measured oxygen saturation and a pulse rate.

One embodiment may further comprise a waveform generator that synthesizes the waveform from a predetermined shape. The waveform generator synthesizes the waveform at a frequency adjusted to be generally equivalent to the pulse rate. The waveform may have a first amplitude and a second amplitude, and the waveform generator may be configured to adjusted the amplitudes so that measurements derived by the monitor are generally equivalent to a measured oxygen saturation.

In another embodiment, the sensor interface is operable on the sensor signal to provide a plethysmograph signal output, where the first baseband signal is responsive to the plethysmograph signal. This embodiment may further comprise a waveform modulator that modifies a decoded signal responsive to the second baseband signal to provide the waveform. The waveform modulator may comprise a demodulator that separates a first signal and a second signal from the decoded signal, an amplifier that adjusts amplitudes of the first and second signals to generate a first adjusted signal and a second adjusted signal, and a modulator that combines the first and second adjusted signals into the waveform. The amplitudes of the first and second signals may be responsive to predetermined calibration data for the sensor and the monitor.

An aspect of a physiological measurement communications adapter method comprises the steps of inputting a sensor signal at a patient location, communicating patient data derived from the sensor signal between the patient location and a monitor location, constructing a waveform at the monitor location responsive to the sensor signal, and providing the waveform to a monitor via a sensor port. The waveform is constructed so that the monitor calculates a parameter generally equivalent to a measurement derivable from the sensor signal.

In one embodiment, the communicating step may comprise the substeps of deriving a conditioned signal from the sensor signal, calculating a parameter signal from the conditioned signal, and transmitting the parameter signal from the patient location to the monitor location. The constructing step may comprise the substep of synthesizing the waveform from the parameter signal. In an alternative embodiment, the communicating step may comprise the substeps of deriving a conditioned signal from said sensor signal and transmitting the conditioned signal from the patient location to the monitor location. The constructing step may comprise the substeps of demodulating the conditioned signal and re-modulating the conditioned signal to generate the waveform. The providing step may comprise the substeps of inputting a monitor signal from an LED drive output of the sensor port, modulating the waveform in response to the monitor signal, and outputting the waveform on a detector input of the sensor port.

Another aspect of a physiological measurement communications adapter comprises a sensor interface means for inputting a sensor signal and outputting a conditioned signal, a transmitter means for sending data responsive to the sensor signal, and a receiver means for receiving the data. The communications adapter further comprises a waveform processor means for constructing a waveform from the data so that measurements derived by a monitor from the waveform are generally equivalent to measurements derivable from the sensor signal, and a monitor interface means for communicating the waveform to a sensor port of the monitor. The communications adapter may further comprise a signal processor means for deriving a parameter signal from the conditioned signal, where the data comprises the parameter signal. The waveform processor means may comprise a means for synthesizing the waveform from the parameter signal. The data may comprise the conditioned signal, and the waveform processor means may comprise a means for modulating the conditioned signal in response to the monitor.

DETAILED DESCRIPTION OF THE PREFERRED EMBODIMENT

Overview

Figure 3:
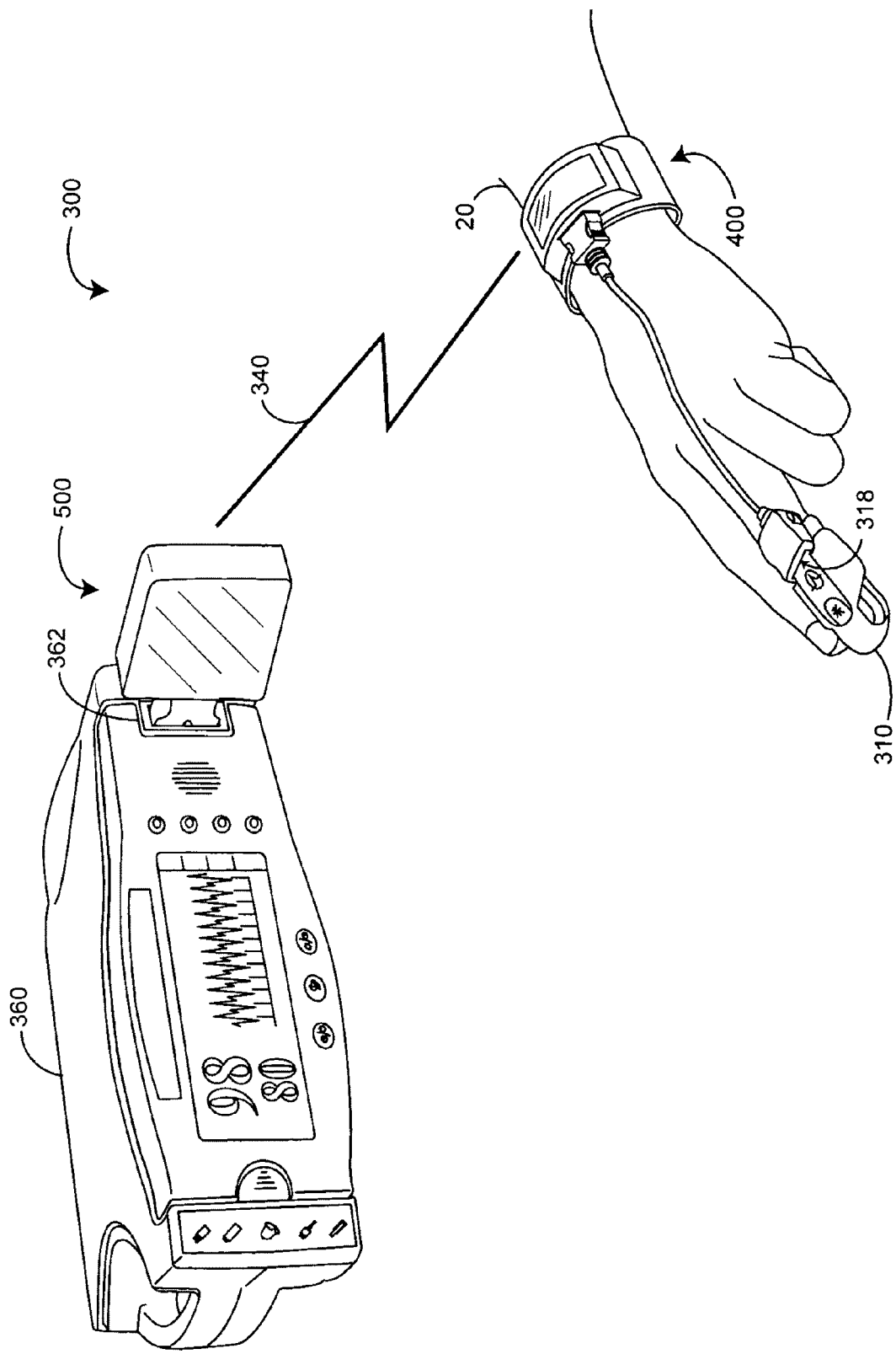
FIG. 3 is an illustration of a physiological measurement communications adapter.
Figure 4A:
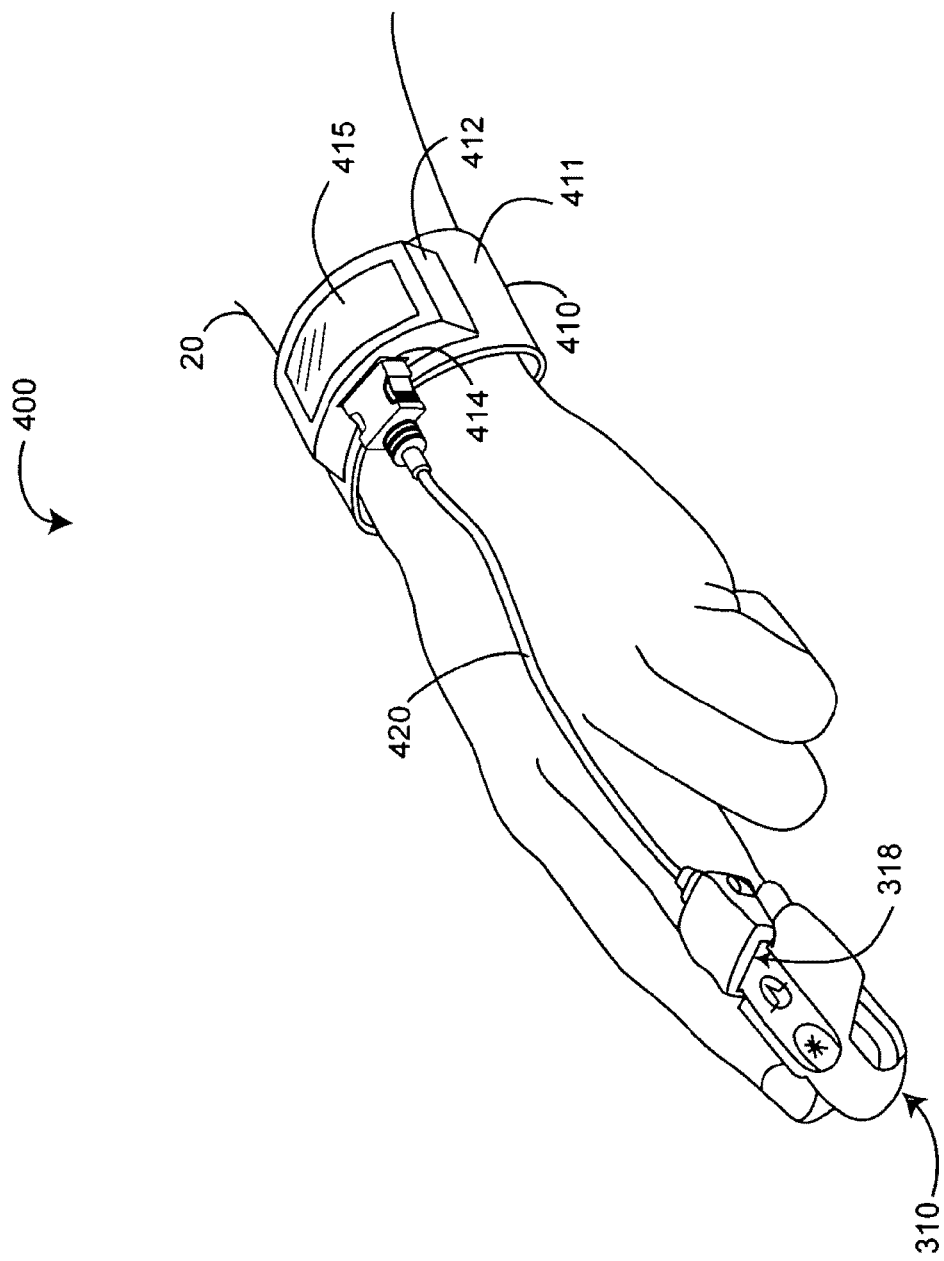
FIGS. 4A-B are illustrations of communications adapter sensor modules.
Figure 4B:
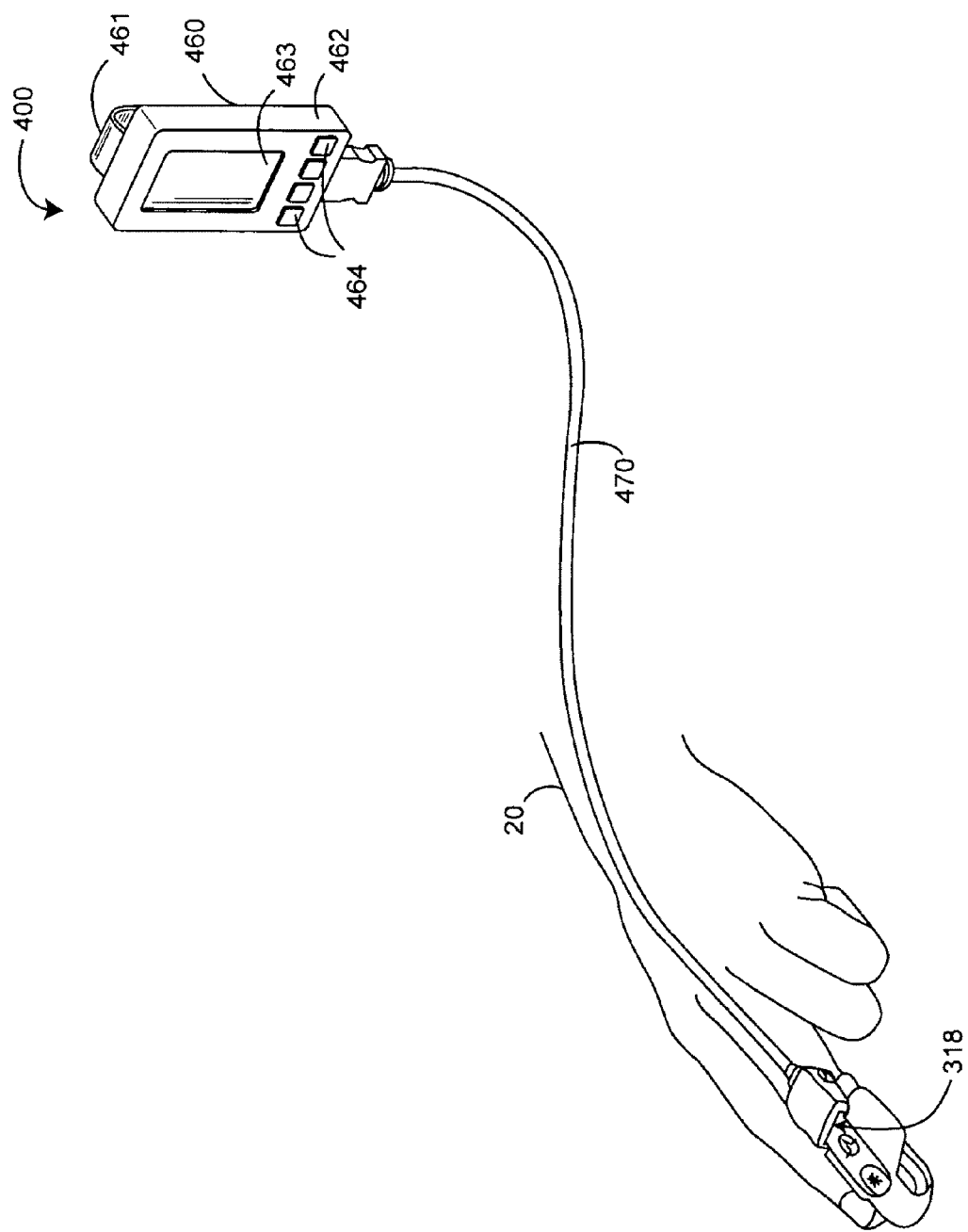
Figure 5A:
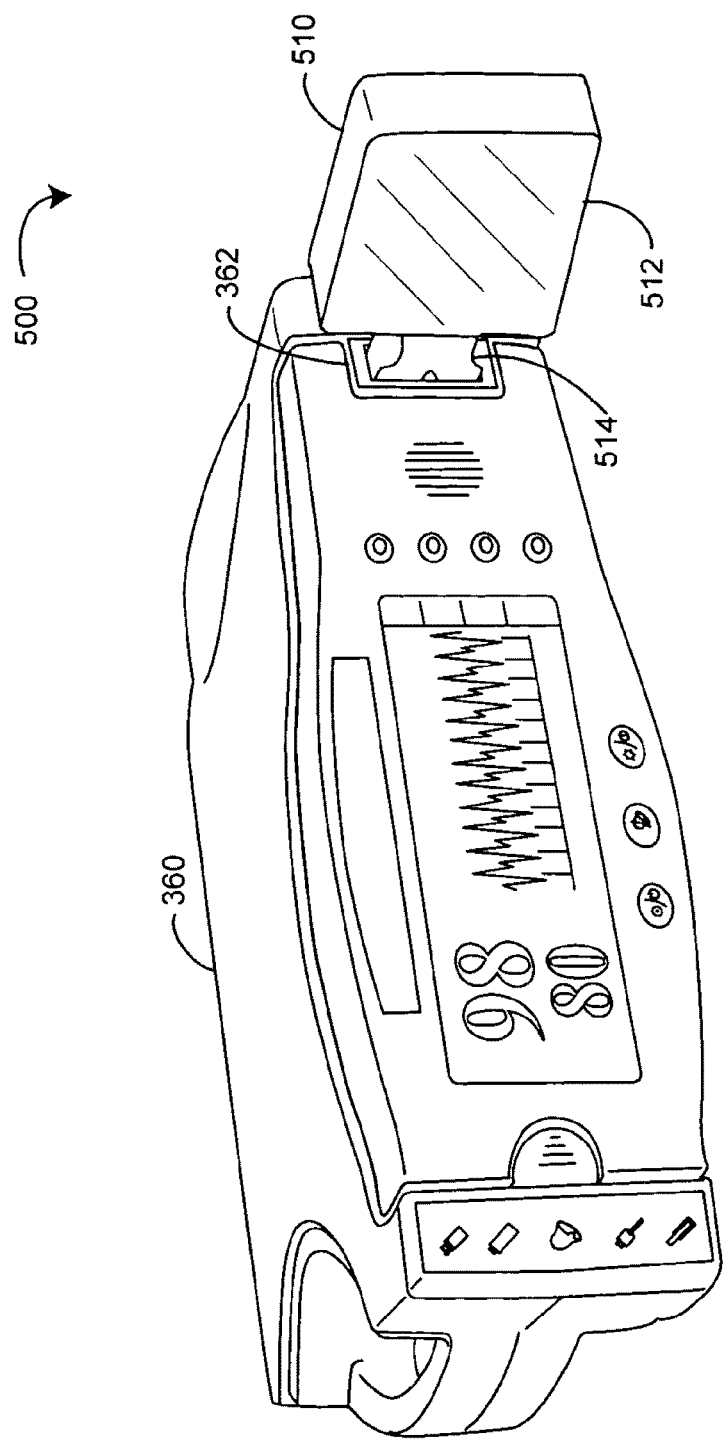
FIGS. 5A-C are illustrations of communications adapter monitor modules.
Figure 5B:
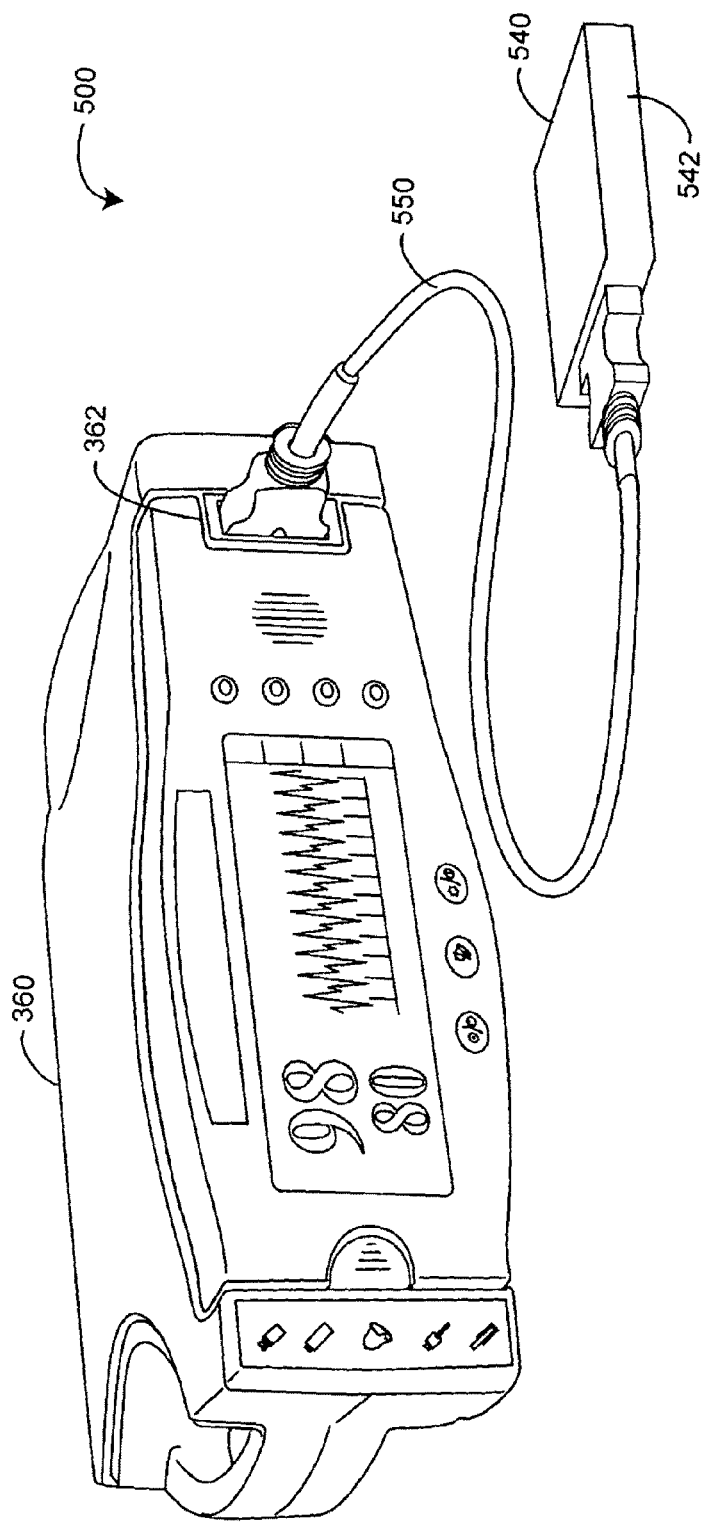
Figure 5C:
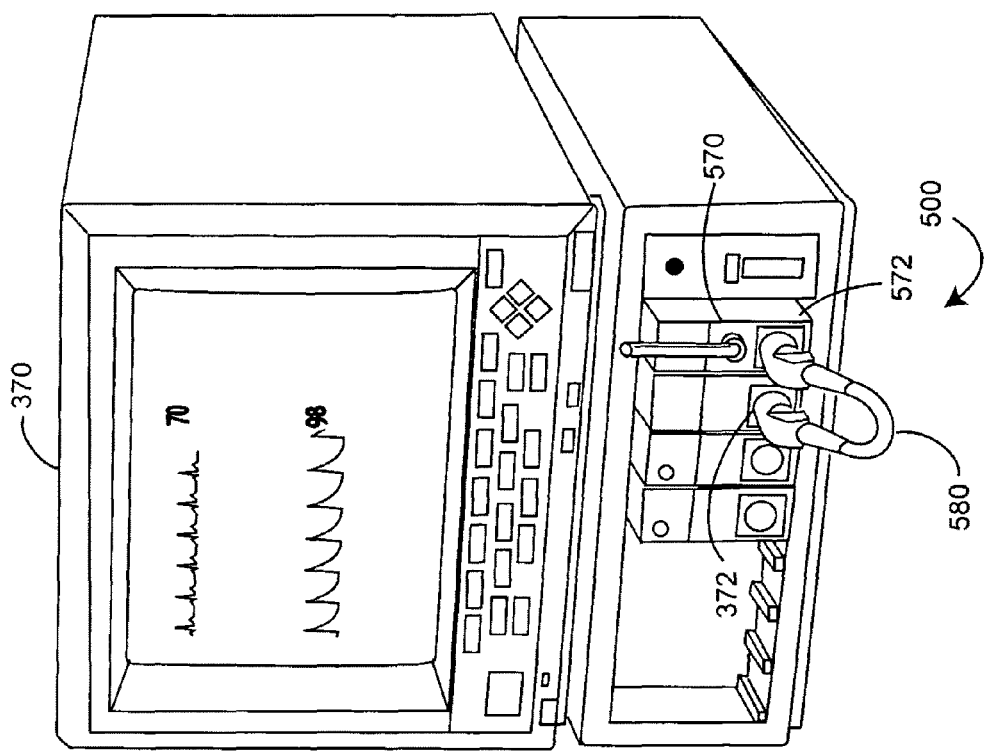
Figure 6:
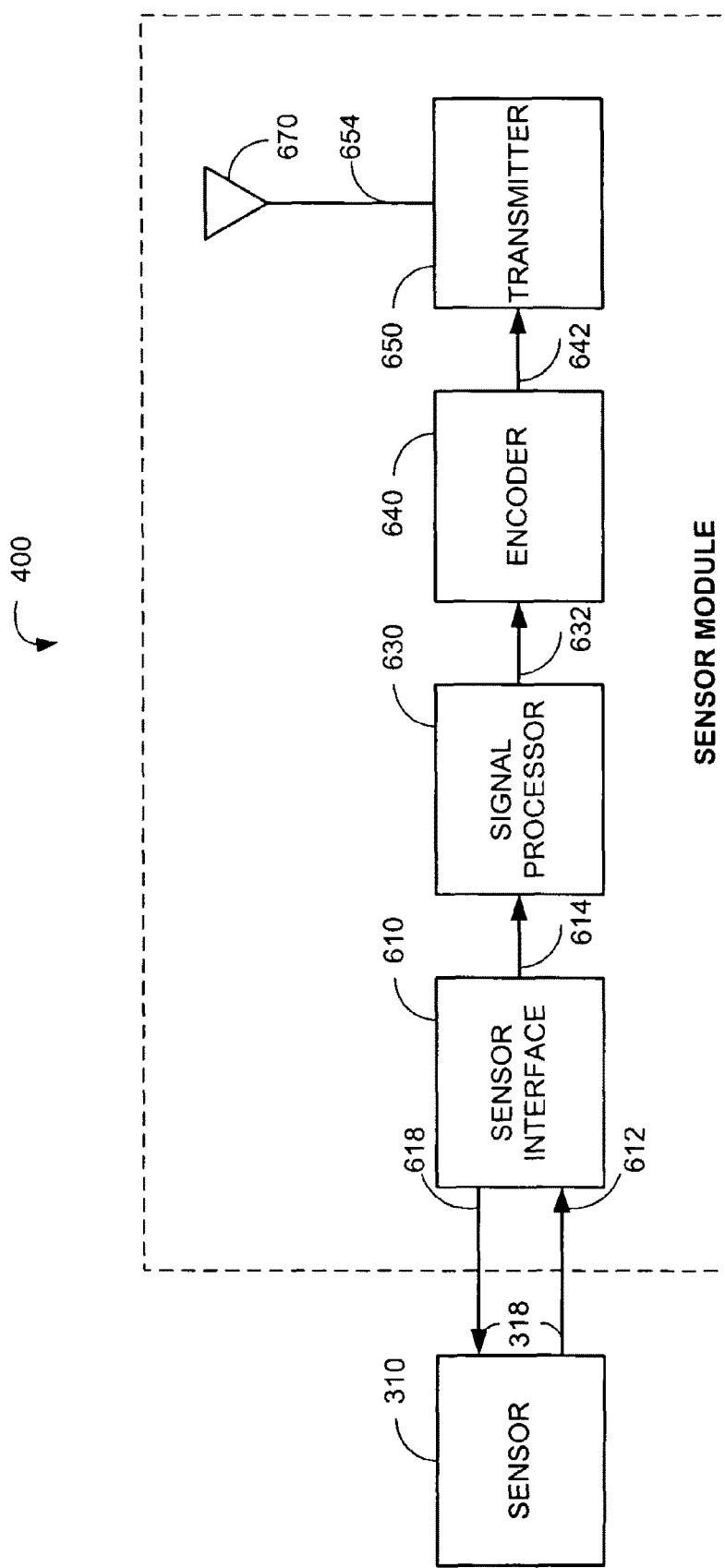
FIG. 6 is a functional block diagram of a communications adapter sensor module.
Figure 7:
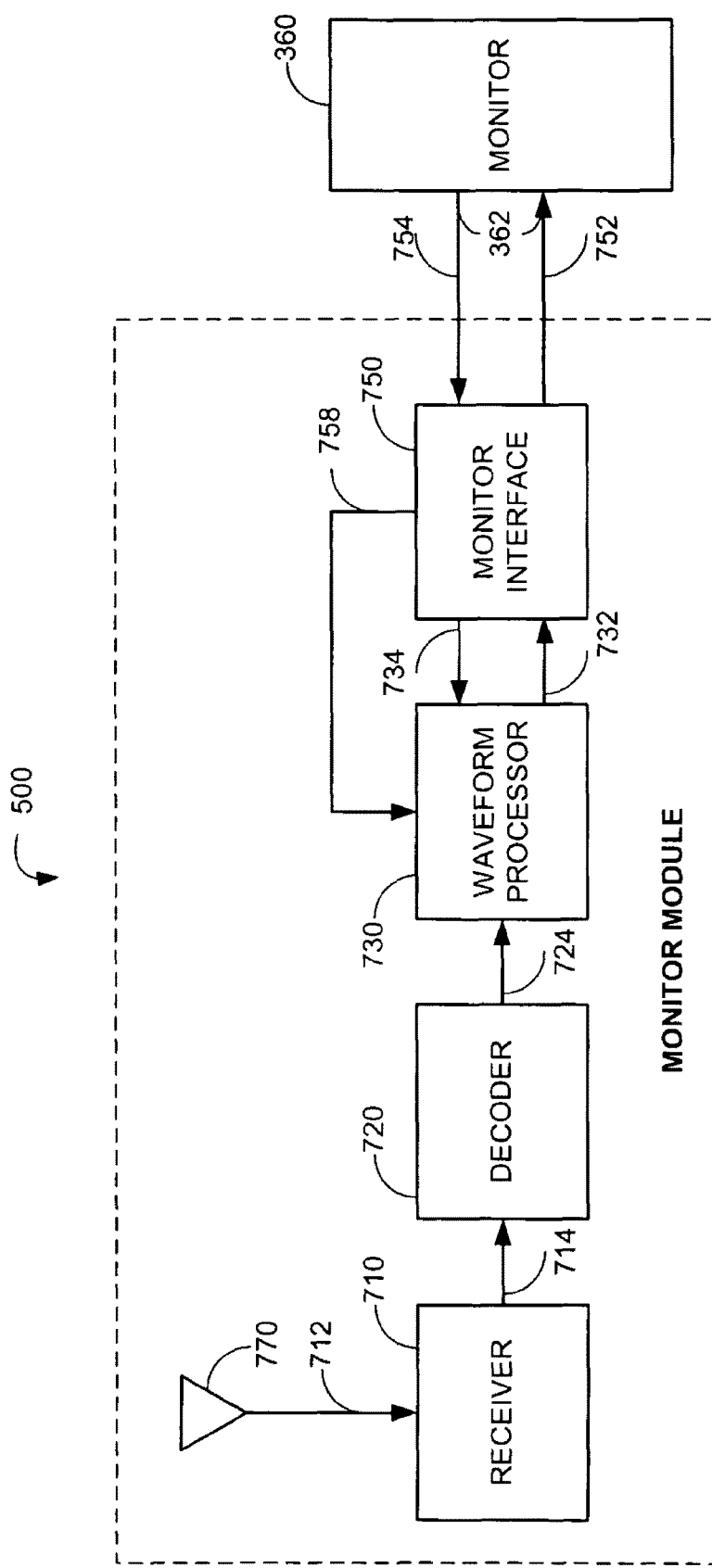
FIG. 7 is a functional block diagram of a communications adapter monitor module.
Figure 8:
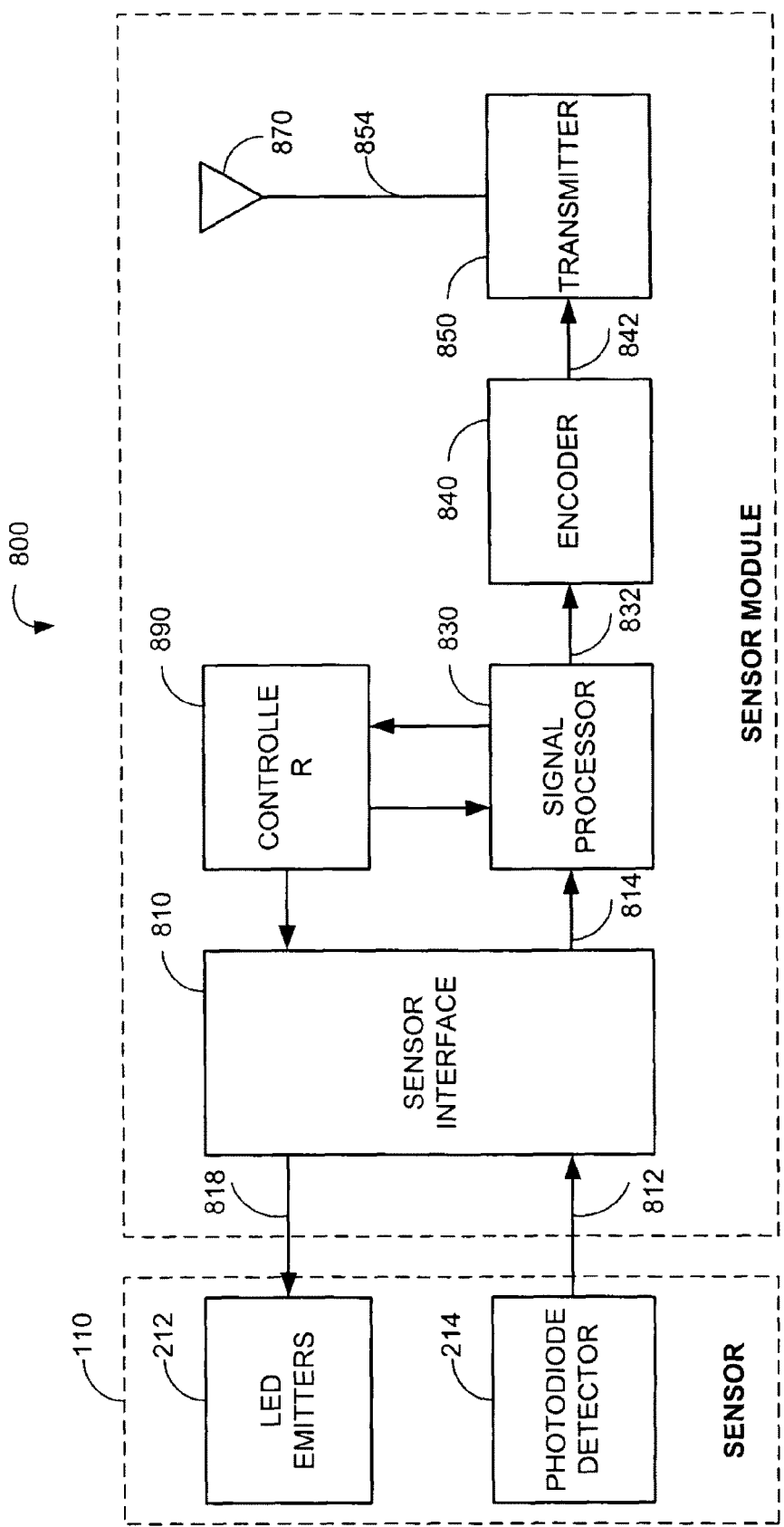
FIG. 8 is a functional block diagram of a sensor module configured to transmit measured pulse oximeter parameters.
Figure 9:
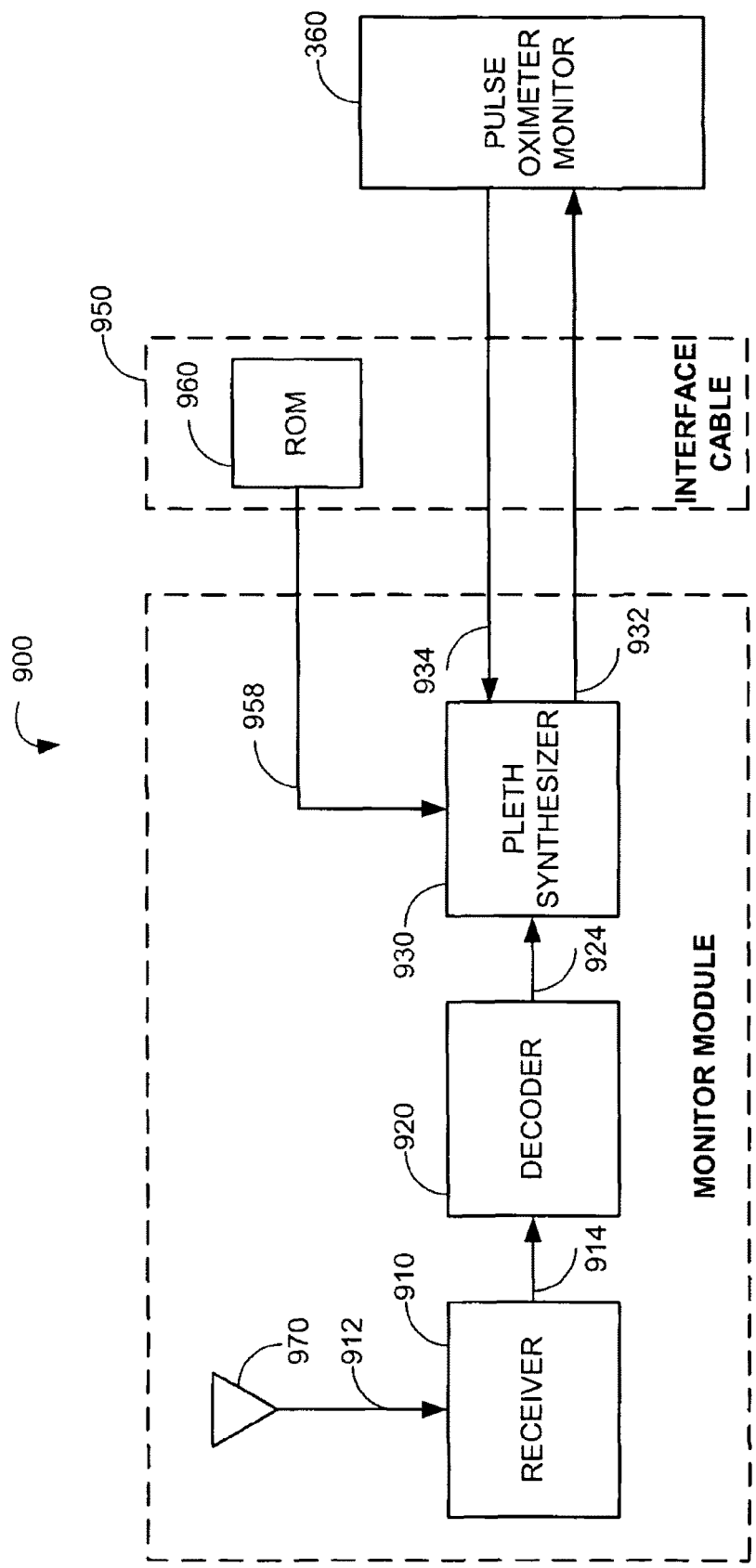
FIG. 9 is a functional block diagram of a monitor module configured to received measured pulse oximeter parameters.
Figure 13:
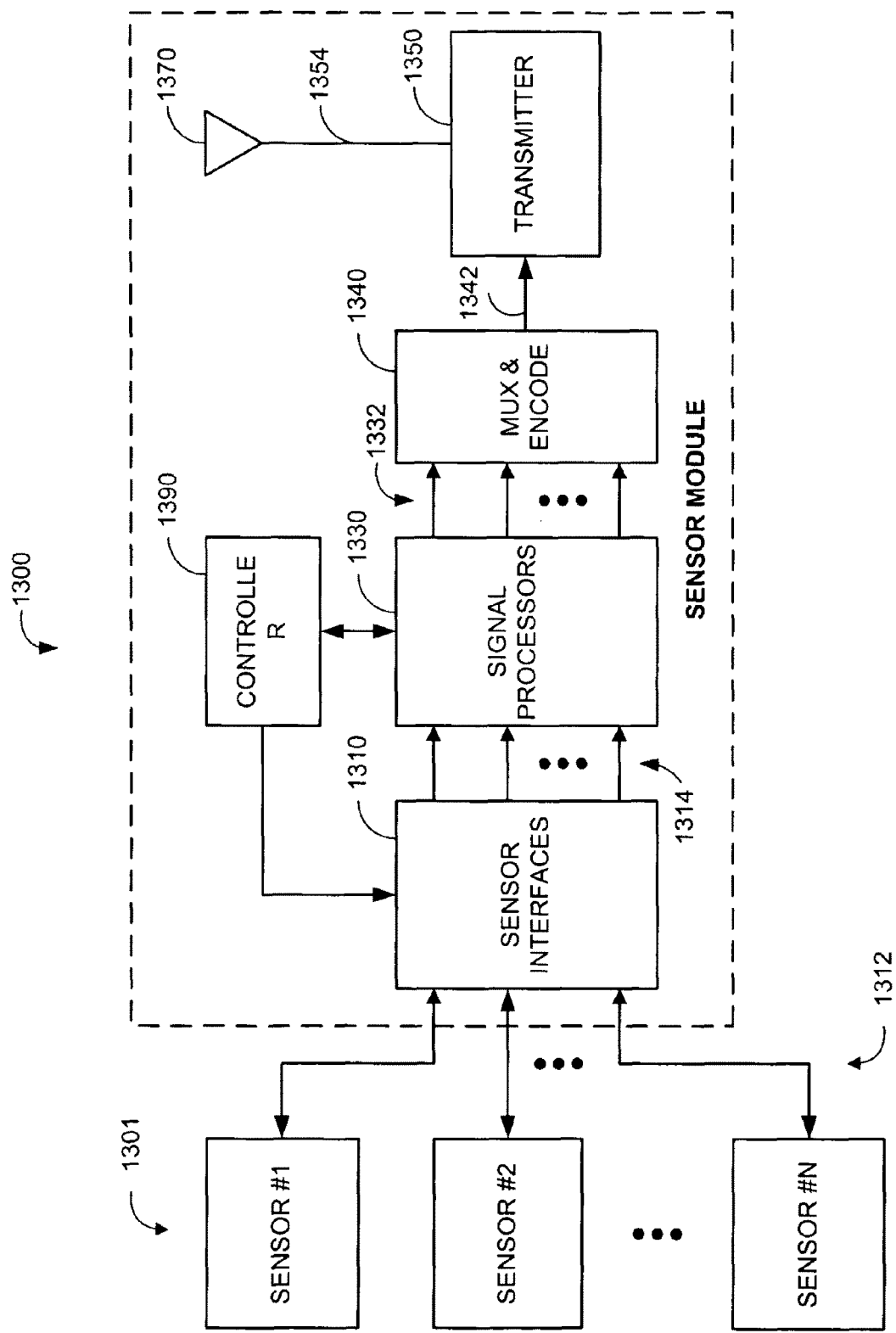
FIG. 13 is a functional block diagram of a sensor module configured for multiple sensors.
Figure 14:
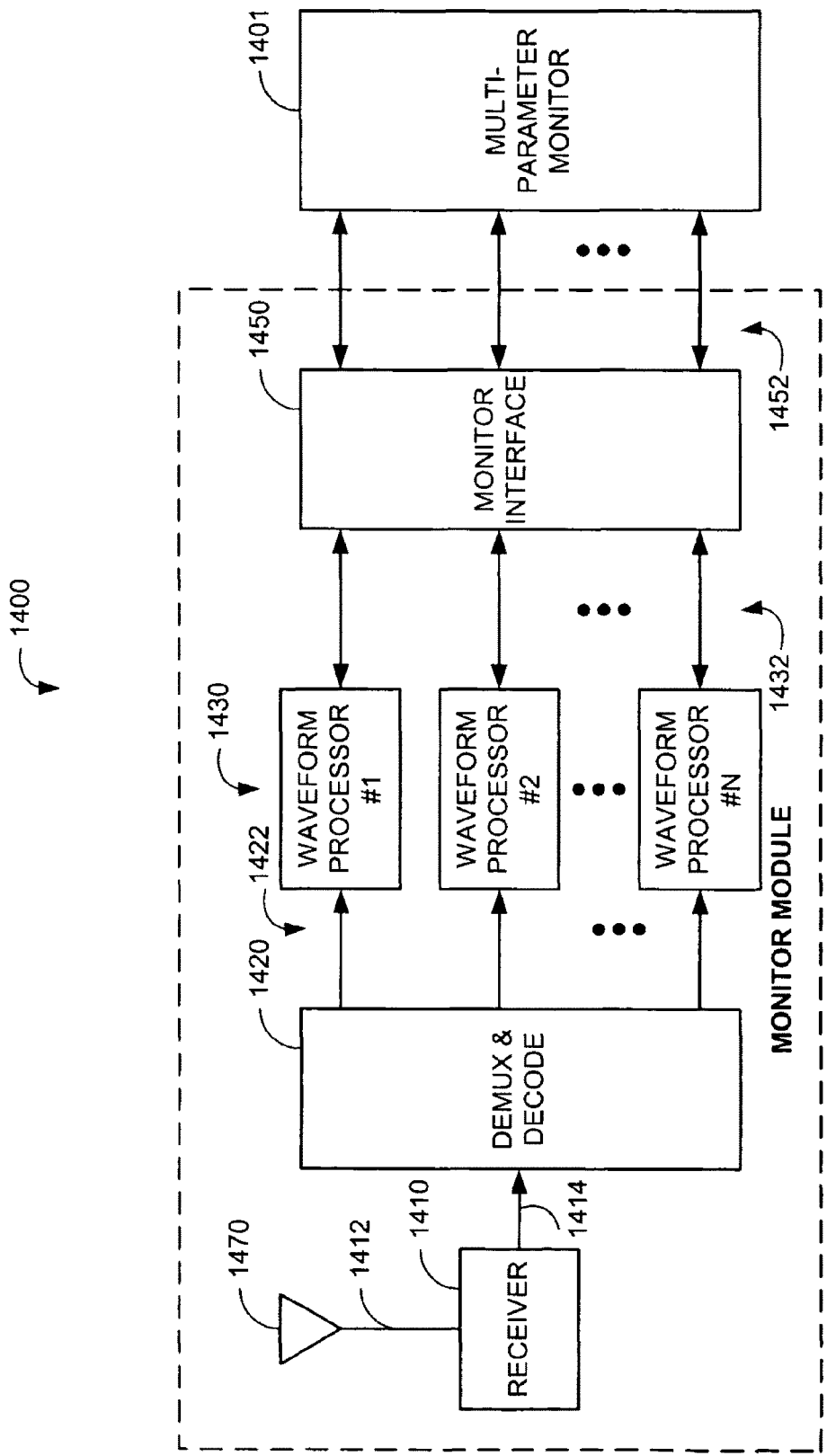
FIG. 14 is a functional block diagram of a monitor module configured for multiple sensors.

FIG. 3 illustrates one embodiment of a communications adapter. FIGS. 4-5 illustrate physical configurations for a communications adapter. In particular, FIGS. 4A-B illustrate sensor module configurations and FIGS. 5A-C illustrate monitor module configurations. FIGS. 6-14 illustrate communications adapter functions. In particular, FIGS. 6-7 illustrate general functions for a sensor module and a monitor module, respectively. FIGS. 8-9 functionally illustrate a communications adapter where derived pulse oximetry parameters, such as saturation and pulse rate are transmitted between a sensor module and a monitor module. Also, FIGS. 10-12 functionally illustrate a communications adapter where a plethysmograph is transmitted between a sensor module and a monitor module. FIGS. 13-14 functionally illustrate a multiple-parameter communications adapter.

Figure 1:
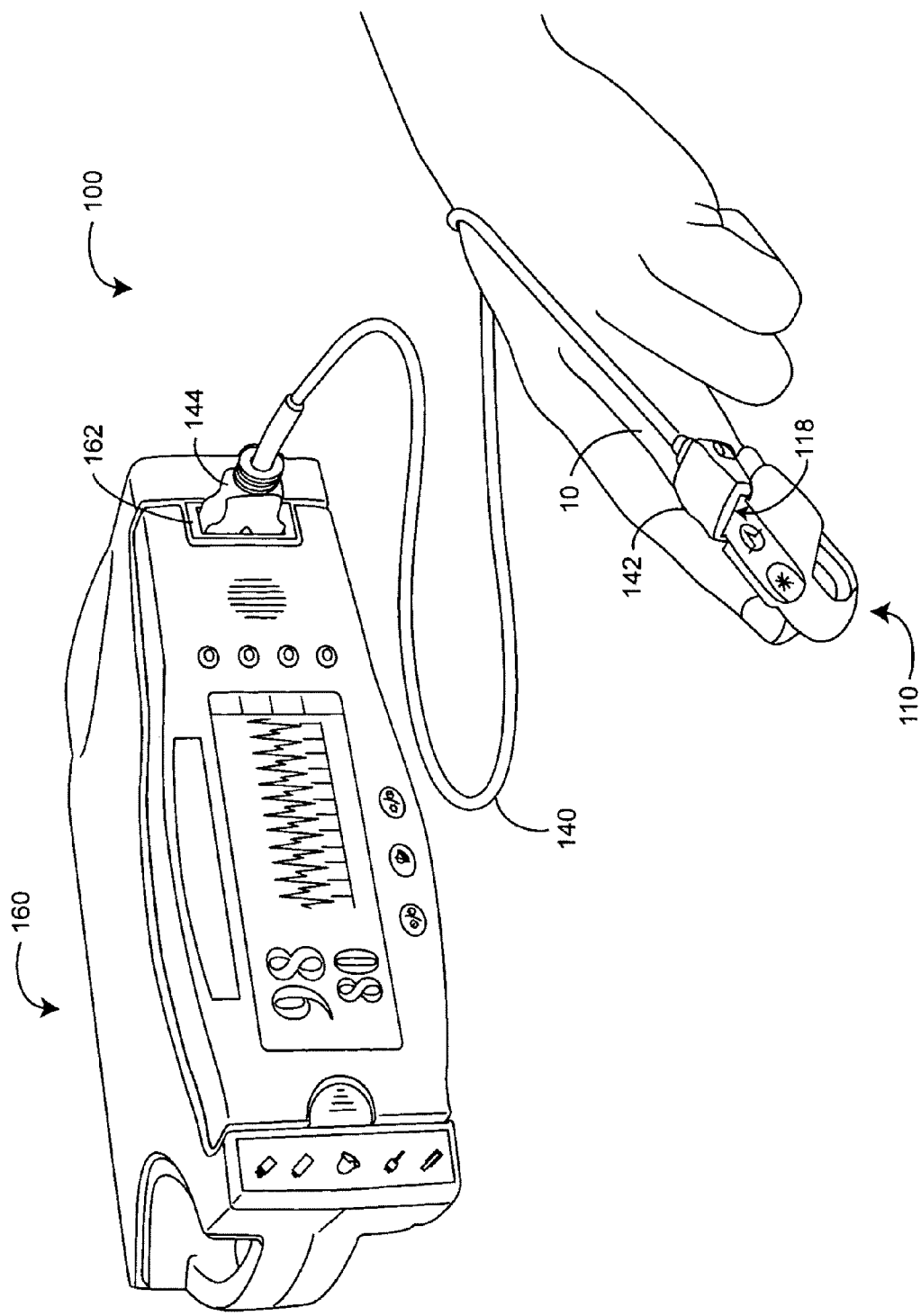
FIG. 1 is an illustration of a prior art pulse oximetry system.

FIG. 3 illustrates a communications adapter 300 having a sensor module 400 and a monitor module 500. The communications adapter 300 communicates patient data derived from a sensor 310 between the sensor module 400, which is located proximate a patient 20 and the monitor module 500, which is located proximate a monitor 360. A wireless link 340 is provided between the sensor module 400 and the monitor module 500, replacing the conventional patient cable, such as a pulse oximetry patient cable 140 (FIG. 1). Advantageously, the sensor module 400 is plug-compatible with a conventional sensor 310. In particular, the sensor connector 318 connects to the sensor module 400 in a similar manner as to a patient cable. Further, the sensor module 400 outputs a drive signal to the sensor 310 and inputs a sensor signal from the sensor 310 in an equivalent manner as a conventional monitor 360. The sensor module 400 may be battery powered or externally powered. External power may be for recharging internal batteries or for powering the sensor module during operation or both.

As shown in FIG. 3, the monitor module 500 is advantageously plug-compatible with a conventional monitor 360. In particular, the monitor's sensor port 362 connects to the monitor module 500 in a similar manner as to a patient cable, such as a pulse oximetry patient cable 140 (FIG. 1). Further, the monitor module 500 inputs a drive signal from the monitor 360 and outputs a corresponding sensor signal to the monitor 360 in an equivalent manner as a conventional sensor 310. As such, the combination sensor module 400 and monitor module 500 provide a plug-compatible wireless replacement for a patient cable, adapting an existing wired physiological measurement system into a wireless physiological measurement system. The monitor module 500 may be battery powered, powered from the monitor, such as by tapping current from a monitor's LED drive, or externally powered from an independent AC or DC power source.

Although a communications adapter 300 is described herein with respect to a pulse oximetry sensor and monitor, one of ordinary skill in the art will recognize that a communications adapter may provide a plug-compatible wireless replace for a patient cable that connects any physiological sensor and corresponding monitor. For example, a communications adapter 300 may be applied to a biopotential sensor, a non-invasive blood pressure (NIBP) sensor, a respiratory rate sensor, a glucose sensor and the corresponding monitors, to name a few.

Sensor Module Physical Configurations

FIGS. 4A-B illustrate physical embodiments of a sensor module 400. FIG. 4A illustrates a wrist-mounted module 410 having a wrist strap 411, a case 412 and an auxiliary cable 420. The case 412 contains the sensor module electronics, which are functionally described with respect to FIG. 6, below. The case 412 is mounted to the wrist strap 411, which attaches the wrist-mounted module 410 to a patient 20. The auxiliary cable 420 mates to a sensor connector 318 and a module connector 414, providing a wired link between a conventional sensor 310 and the wrist-mounted module 410. Alternatively, the auxiliary cable 420 is directly wired to the sensor module 400. The wrist-mounted module 410 may have a display 415 that shows sensor measurements, module status and other visual indicators, such as monitor status. The wrist-mounted module 410 may also have keys (not shown) or other input mechanisms to control its operational mode and characteristics. In an alternative embodiment, the sensor 310 may have a tail (not shown) that connects directly to the wrist-mounted module 410, eliminating the auxiliary cable 420.

FIG. 4B illustrates a clip-on module 460 having a clip 461, a case 462 and an auxiliary cable 470. The clip 461 attaches the clip-on module 460 to patient clothing or objects near a patient 20, such as a bed frame. The auxiliary cable 470 mates to the sensor connector 318 and functions as for the auxiliary cable 420 (FIG. 4A) of the wrist-mounted module 410 (FIG. 4A), described above. The clip-on module 460 may have a display 463 and keys 464 as for the wrist-mounted module 410 (FIG. 4A). Either the wrist-mounted module 410 or the clip-on module 460 may have other input or output ports (not shown) that download software, configure the module, or provide a wired connection to other measurement instruments or computing devices, to name a few examples.

Monitor Module Physical Configurations

FIGS. 5A-C illustrate physical embodiments of a monitor module 500. FIG. 5A illustrates a direct-connect module 510 having a case 512 and an integrated monitor connector 514. The case 512 contains the monitor module electronics, which are functionally described with respect to FIG. 7, below. The monitor connector 514 mimics that of the monitor end of a patient cable, such as a pulse oximetry patient cable 140 (FIG. 1), and electrically and mechanically connects the monitor module 510 to the monitor 360 via the monitor's sensor port 362.

FIG. 5B illustrates a cable-connect module 540 having a case 542 and an auxiliary cable 550. The case 542 functions as for the direct-connect module 510 (FIG. 5A), described above. Instead of directly plugging into the monitor 360, the cable-connect module 540 utilizes the auxiliary cable 550, which mimics the monitor end of a patient cable, such as a pulse oximetry patient cable 140 (FIG. 1), and electrically connects the cable-connect module 540 to the monitor sensor port 362.

FIG. 5C illustrates a plug-in module 570 having a plug-in case 572 and an auxiliary cable 580. The plug-in case 572 is mechanically compatible with the plug-in chassis of a multiparameter monitor 370 and may or may not electrically connect to the chassis backplane. The auxiliary cable 580 mimics a patient cable and electrically connects the plug-in module 570 to the sensor port 372 of another plug-in device. A direct-connect module 510 (FIG. 5A) or a cable-connect module 540 (FIG. 5B) may also be used with a multiparameter monitor 370.

In a multiparameter embodiment, such as described with respect to FIGS. 13-14, below, a monitor module 500 may connect to multiple plug-in devices of a multiparameter monitor 370. For example, a cable-connect module 540 (FIG. 5B) may have multiple auxiliary cables 550 (FIG. 5B) that connect to multiple plug-in devices installed within a multiparameter monitor chassis. Similarly, a plug-in module 570 may have one or more auxiliary cables 580 with multiple connectors for attaching to the sensor ports 372 of multiple plug-in devices.

Communications Adapter Functions

FIGS. 6-7 illustrate functional embodiments of a communications adapter. FIG. 6 illustrates a sensor module 400 having a sensor interface 610, a signal processor 630, an encoder 640, a transmitter 650 and a transmitting antenna 670. A physiological sensor 310 provides an input sensor signal 612 at the sensor connector 318. Depending on the sensor 310, the sensor module 400 may provide one or more drive signals 618 to the sensor 310. The sensor interface 610 inputs the sensor signal 612 and outputs a conditioned signal 614. The conditioned signal 614 may be coupled to the transmitter 650 or further processed by a signal processor 630. If the sensor module configuration utilizes a signal processor 630, it derives a parameter signal 632 responsive to the sensor signal 612, which is then coupled to the transmitter 650. Regardless, the transmitter 650 inputs a baseband signal 642 that is responsive to the sensor signal 612. The transmitter 650 modulates the baseband signal 642 with a carrier to generate a transmit signal 654. The transmit signal 654 may be derived by various amplitude, frequency or phase modulation schemes, as is well known in the art. The transmit signal 654 is coupled to the transmit antenna 670, which provides wireless communications to a corresponding receive antenna 770 (FIG. 7), as described below.

As shown in FIG. 6, the sensor interface 610 conditions and digitizes the sensor signal 612 to generate the conditioned signal 614. Sensor signal conditioning may be performed in the analog domain or digital domain or both and may include amplification and filtering in the analog domain and filtering, buffering and data rate modification in the digital domain, to name a few. The resulting conditioned signal 614 is responsive to the sensor signal 612 and may be used to calculate or derive a parameter signal 632.

Further shown in FIG. 6, the signal processor 630 performs signal processing on the conditioned signal 614 to generate the parameter signal 632. The signal processing may include buffering, digital filtering, smoothing, averaging, adaptive filtering and frequency transforms to name a few. The resulting parameter signal 632 may be a measurement calculated or derived from the conditioned signal, such as oxygen saturation, pulse rate, blood glucose, blood pressure and EKG to name a few. Also, the parameter signal 632 may be an intermediate result from which the above-stated measurements may be calculated or derived.

As described above, the sensor interface 610 performs mixed analog and digital pre-processing of an analog sensor signal and provides a digital output signal to the signal processor 630. The signal processor 630 then performs digital post-processing of the front-end processor output. In alternative embodiments, the input sensor signal 612 and the output conditioned signal 614 may be either analog or digital, the front-end processing may be purely analog or purely digital, and the back-end processing may be purely analog or mixed analog or digital.

In addition, FIG. 6 shows an encoder 640, which translates a digital word or serial bit stream, for example, into the baseband signal 642, as is well-known in the art. The baseband signal 642 comprises the symbol stream that drives the transmit signal 654 modulation, and may be a single signal or multiple related signal components, such as in-phase and quadrature signals. The encoder 640 may include data compression and redundancy, also well-known in the art.

FIG. 7 illustrates a monitor module 500 having a receive antenna 770, a receiver 710, a decoder 720, a waveform processor 730 and a monitor interface 750. A receive signal 712 is coupled from the receive antenna 770, which provides wireless communications to a corresponding transmit antenna 670 (FIG. 6), as described above. The receiver 710 inputs the receive signal 712, which corresponds to the transmit signal 654 (FIG. 6). The receiver 710 demodulates the receive signal to generate a baseband signal 714. The decoder 720 translates the symbols of the demodulated baseband signal 714 into a decoded signal 724, such as a digital word stream or bit stream. The waveform processor 730 inputs the decoded signal 724 and generates a constructed signal 732. The monitor interface 750 is configured to communicate the constructed signal 732 to a sensor port 362 of a monitor 360. The monitor 360 may output a sensor drive signal 754, which the monitor interface 750 inputs to the waveform processor 730 as a monitor drive signal 734. The waveform processor 730 may utilize the monitor drive signal 734 to generate the constructed signal 732. The monitor interface 750 may also provide characterization information 758 to the waveform processor 730, relating to the monitor 360, the sensor 310 or both, that the waveform processor 730 utilizes to generate the constructed signal 732.

The constructed signal 732 is adapted to the monitor 360 so that measurements derived by the monitor 360 from the constructed signal 732 are generally equivalent to measurements derivable from the sensor signal 612 (FIG. 6). Note that the sensor 310 (FIG. 6) may or may not be directly compatible with the monitor 360. If the sensor 310 (FIG. 6) is compatible with the monitor 360, the constructed signal 732 is generated so that measurements derived by the monitor 360 from the constructed signal 732 are generally equivalent (within clinical significance) with those derivable directly from the sensor signal 612 (FIG. 6). If the sensor 310 (FIG. 6) is not compatible with the monitor 360, the constructed signal 732 is generated so that measurements derived by the monitor 360 from the constructed signal 732 are generally equivalent to those derivable directly from the sensor signal 612 (FIG. 6) using a compatible monitor.

Wireless Pulse Oximetry

Figure 10:
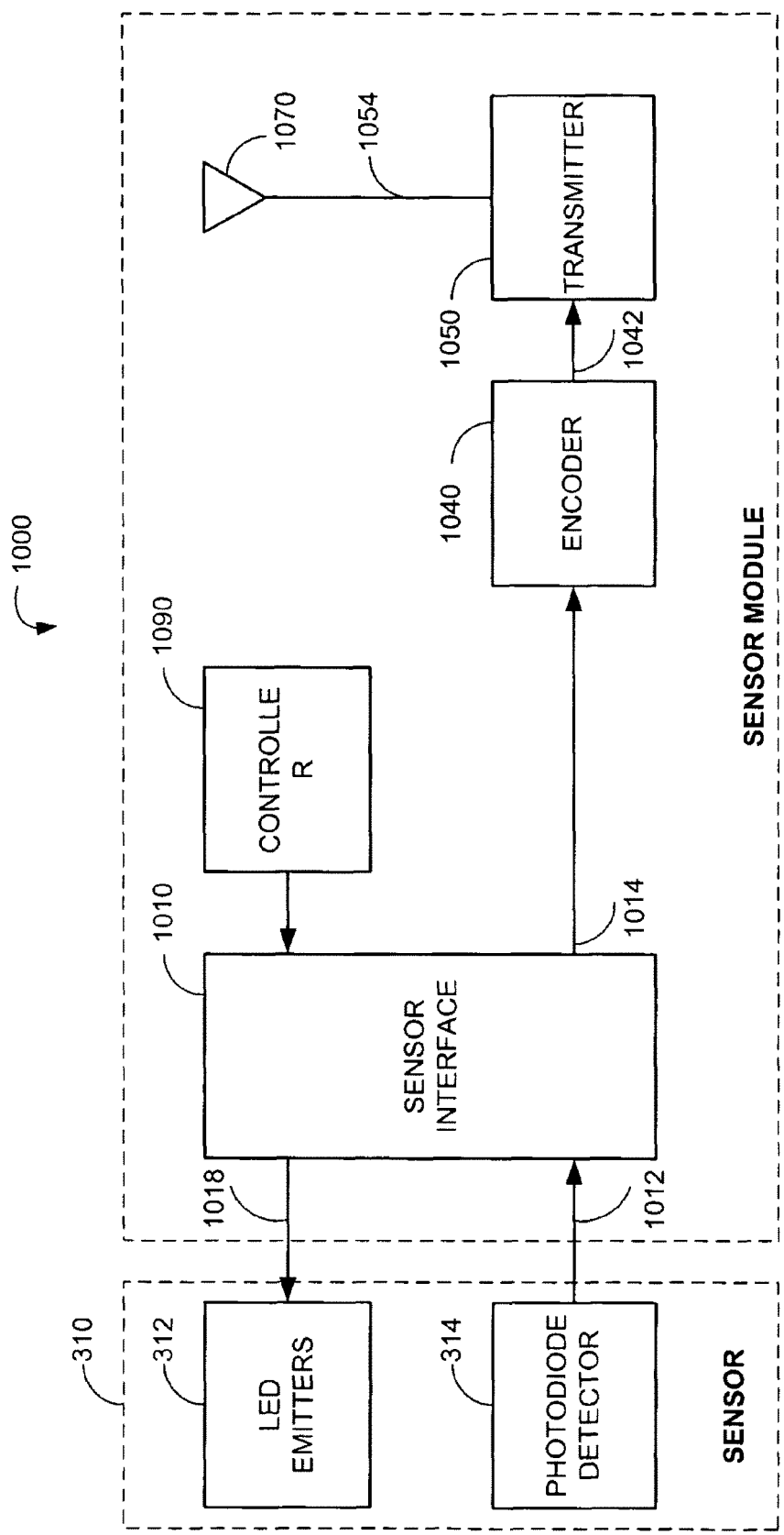
FIG. 10 is a functional block diagram of a sensor module configured to transmit a plethysmograph.
Figure 11:
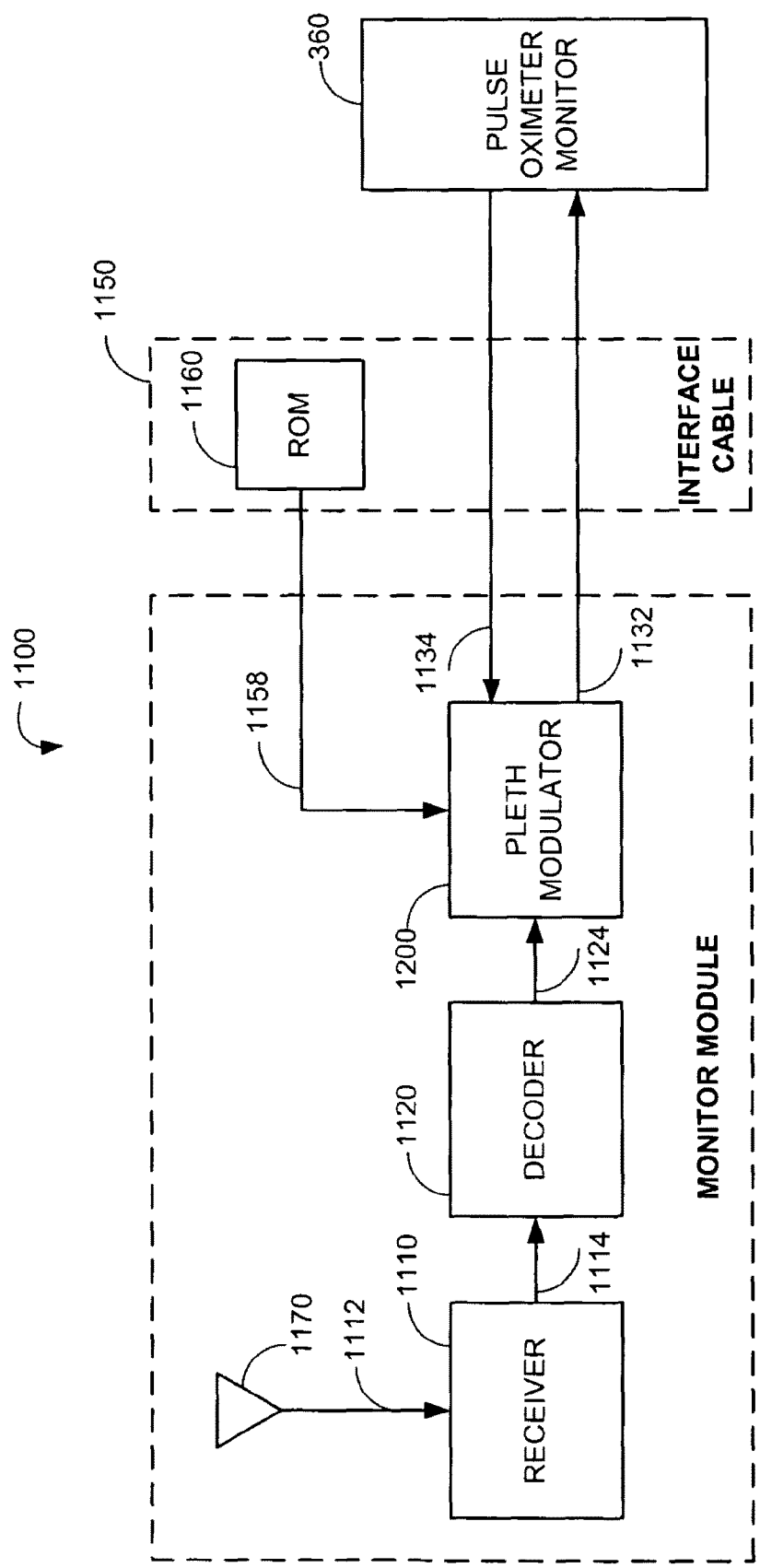
FIG. 11 is a functional block diagram of a monitor module configured to receive a plethysmograph.

FIGS. 8-11 illustrate pulse oximeter embodiments of a communications adapter. FIGS. 8-9 illustrate a sensor module and a monitor module, respectively, configured to communicate measured pulse oximeter parameters. FIG. 10-11 illustrate a sensor module and a monitor module, respectively, configured to communicate a plethysmograph signal.

Parameter Transmission

Figure 2:
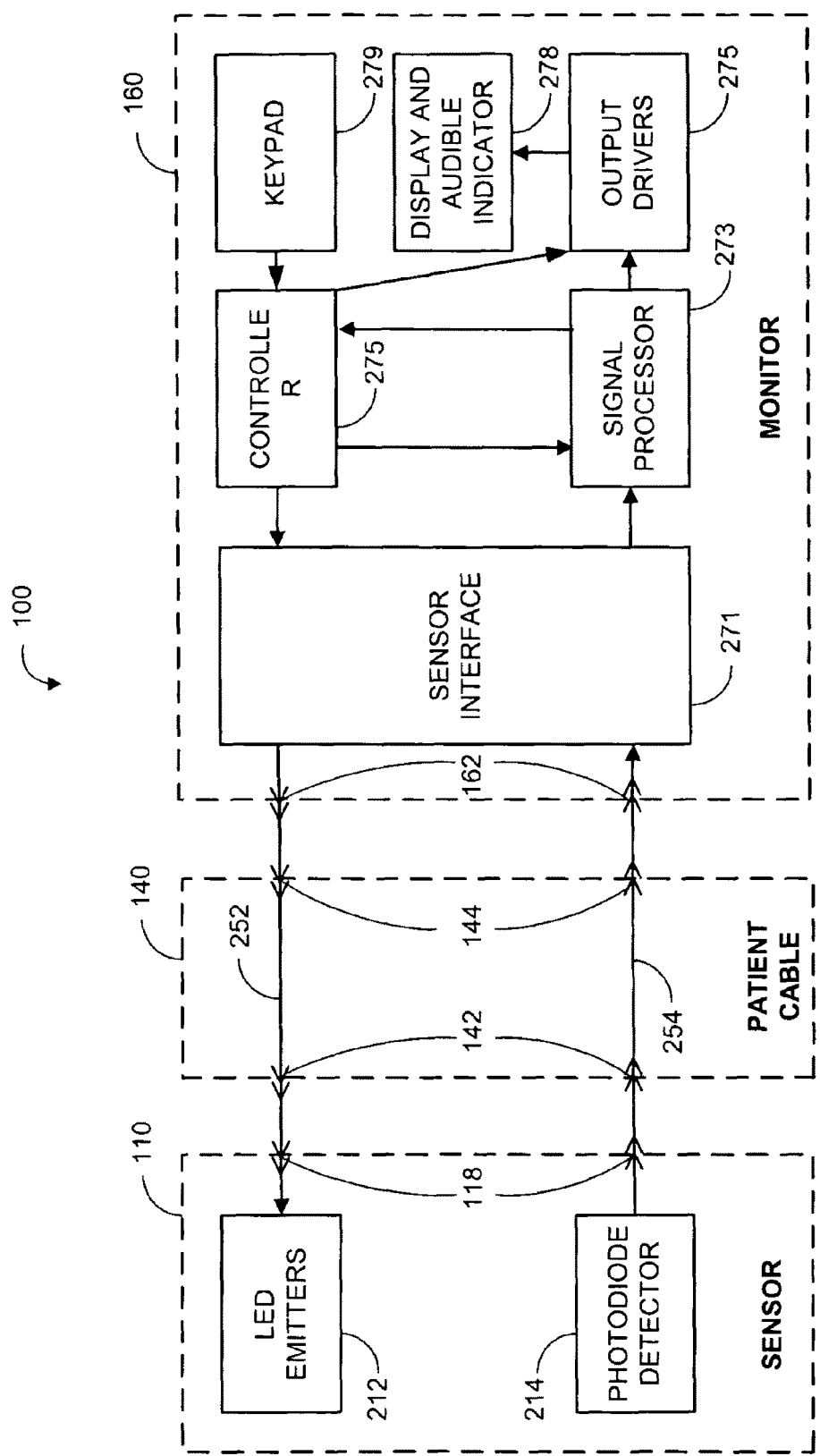
FIG. 2 is a functional block diagram of a prior art pulse oximetry system.

FIG. 8 illustrates a pulse oximetry sensor module 800 having a sensor interface 810, signal processor 830, encoder 840, transmitter 850, transmitting antenna 870 and controller 890. The sensor interface 810, signal processor 830 and controller 890 function as described with respect to FIG. 2, above. The sensor interface 810 communicates with a standard pulse oximetry sensor 310, providing an LED drive signal 818 to the LED emitters 312 and receiving a sensor signal 812 from the detector 314 in response. The sensor interface 810 provides front-end processing of the sensor signal 812, also described above, providing a plethysmograph signal 814 to the signal processor 830. The signal processor 830 then derives a parameter signal 832 that comprises a real time measurement of oxygen saturation and pulse rate. The parameter signal 832 may include other parameters, such as measurements of perfusion index and signal quality. In one embodiment, the signal processor is an MS-5 or MS-7 board available from Masimo Corporation, Irvine, Calif.

As shown in FIG. 8, the encoder 840, the transmitter 850 and the transmitting antenna 870 function as described with respect to FIG. 6, above. For example, the parameter signal 832 may be a digital word stream that is serialized into a bit stream and encoded into a baseband signal 842. The baseband signal 842 may be, for example, two bit symbols that drive a quadrature phase shift keyed (QPSK) modulator in the transmitter 850. Other encodings and modulations are also applicable, as described above. The transmitter 850 inputs the baseband signal 842 and generates a transmit signal 854 that is a modulated carrier having a frequency suitable for short-range transmission, such as within a hospital room, doctor's office, emergency vehicle or critical care ward, to name a few. The transmit signal 854 is coupled to the transmit antenna 870, which provides wireless communications to a corresponding receive antenna 970 (FIG. 9), as described below.

FIG. 9 illustrates a monitor module 900 having a receive antenna 970, a receiver 910, a decoder 920, a waveform generator 930 and an interface cable 950. The receive antenna 970, receiver 910 and decoder 920 function as described with respect to FIG. 7, above. In particular, the receive signal 912 is coupled from the receive antenna 970, which provides wireless communications to a corresponding transmit antenna 870 (FIG. 8). The receiver 910 inputs the receive signal 912, which corresponds to the transmit signal 854 (FIG. 8). The receiver 810 demodulates the receive signal 912 to generate a baseband signal 914. Not accounting for transmission errors, the baseband signal 914 corresponds to the sensor module baseband signal 842 (FIG. 8), for example a symbol stream of two bits each. The decoder 920 assembles the baseband signal 914 into a parameter signal 924, which, for example, may be a sequence of digital words corresponding to oxygen saturation and pulse rate. Again, not accounting for transmission errors, the monitor module parameter signal 924 corresponds to the sensor module parameter signal 832 (FIG. 8), derived by the signal processor 830 (FIG. 8).

Also shown in FIG. 9, the waveform generator 930 is a particular embodiment of the waveform processor 730 (FIG. 7) described above. The waveform generator 930 generates a synthesized waveform 932 that the pulse oximeter monitor 360 can process to calculate $SpO_2$ and pulse rate values or exception messages. In the present embodiment, the waveform generator output does not reflect a physiological waveform. In particular, the synthesized waveform is not physiological data from the sensor module 800, but is a waveform synthesized from predetermined stored waveform data to cause the monitor 360 to calculate oxygen saturation and pulse rate equivalent to or generally equivalent (within clinical significance) to that calculated by the signal processor 830 (FIG. 8). The actual intensity signal from the patient received by the detector 314 (FIG. 8) is not provided to the monitor 360 in the present embodiment. Indeed, the waveform provided to the monitor 360 will usually not resemble a plethysmographic waveform or other physiological data from the patient to whom the sensor module 800 (FIG. 8) is attached.

The synthesized waveform 932 is modulated according to the drive signal input 934. That is, the pulse oximeter monitor 360 expects to receive a red and IR modulated intensity signal originating from a detector, as described with respect to FIGS. 1-2, above. The waveform generator 930 generates the synthesized waveform 932 with a predetermined shape, such as a triangular or sawtooth waveform stored in waveform generator memory or derived by a waveform generator algorithm. The waveform is modulated synchronously with the drive input 934 with first and second amplitudes that are processed in the monitor 360 as red and IR portions of a sensor signal. The frequency and the first and second amplitudes are adjusted so that pulse rate and oxygen saturation measurements derived by the pulse oximeter monitor 360 are generally equivalent to the parameter measurements derived by the signal processor 830 (FIG. 8), as described above. One embodiment of a waveform generator 930 is described in U.S. Patent Application No. 60/117,097 entitled "Universal/Upgrading Pulse Oximeter," assigned to Masimo Corporation, Irvine, Calif. and incorporated by reference herein. Although the waveform generator 930 is described above as synthesizing a waveform that does not resemble a physiological signal, one of ordinary skill will recognize that another embodiment of the waveform generator 930 could incorporate, for example, a plethysmograph simulator or other physiological signal simulator.

Further shown in FIG. 9, the interface cable 950 functions in a manner similar to the monitor interface 750 (FIG. 7) described above. The interface cable 950 is configured to communicate the synthesized waveform 932 to the monitor 360 sensor port and to communicate the sensor drive signal 934 to the waveform generator 930. The interface cable 950 may include a ROM 960 that contains monitor and sensor characterization data. The ROM 960 is read by the waveform generator 930 so that the synthesized waveform 932 is adapted to a particular monitor 360. For example, the ROM 960 may contain calibration data of red/IR versus oxygen saturation, waveform amplitude and waveform shape information. An interface cable is described in U.S. Patent Application No. 60/117,092, referenced above. Monitor-specific SatShare™ brand interface cables are available from Masimo Corporation, Irvine, Calif. In an alternative embodiment, such as a direct connect monitor module as illustrated in FIG. 5A, an interface cable 950 is not used and the ROM 960 may be incorporated within the monitor module 900 itself.

Plethysmograph Transmission

FIG. 10 illustrates another pulse oximetry sensor module 1000 having a sensor interface 1010, encoder 1040, transmitter 1050, transmitting antenna 1070 and controller 1090, which have the corresponding functions as those described with respect to FIG. 8, above. The encoder 1040, however, inputs a plethysmograph signal 1014 rather than oxygen saturation and pulse rate measurements 832 (FIG. 8). Thus, the sensor module 1000 according to this embodiment encodes and transmits a plethysmograph signal 1014 to a corresponding monitor module 1100 (FIG. 11) in contrast to derived physiological parameters, such as oxygen saturation and pulse rate. The plethysmograph signal 1014 is illustrated in FIG. 10 as being a direct output from the sensor interface 1010. In another embodiment, the sensor module 1000 incorporates a decimation processor, not shown, after the sensor interface 1010 so as to provide a plethysmograph signal 1014 having a reduced sample rate.

FIG. 11 illustrates another pulse oximetry monitor module 1100 having a receive antenna 1170, a receiver 1110, a decoder 1120 and an interface cable 1150, which have the corresponding functions as those described with respect to FIG. 9, above. This monitor module embodiment 1100, however, has a waveform modulator 1200 rather than a waveform generator 930 (FIG. 9), as described above. The waveform modulator 1200 inputs a plethysmograph signal from the decoder 1120 rather than oxygen saturation and pulse rate measurements, as described with respect to FIG. 9, above. Further, the waveform modulator 1200 provides an modulated waveform 1132 to the pulse oximeter monitor 360 rather than a synthesized waveform, as described with respect to FIG. 9. The modulated waveform 1132 is a plethysmographic waveform modulated according to the monitor drive signal input 1134. That is, the waveform modulator 1200 does not synthesize a waveform, but rather modifies the received plethysmograph signal 1124 to cause the monitor 360 to calculate oxygen saturation and pulse rate generally equivalent (within clinical significance) to that derivable by a compatible, calibrated pulse oximeter directly from the sensor signal 1012 (FIG. 10). The waveform modulator 1200 is described in further detail with respect to FIG. 12, below.

Figure 12:
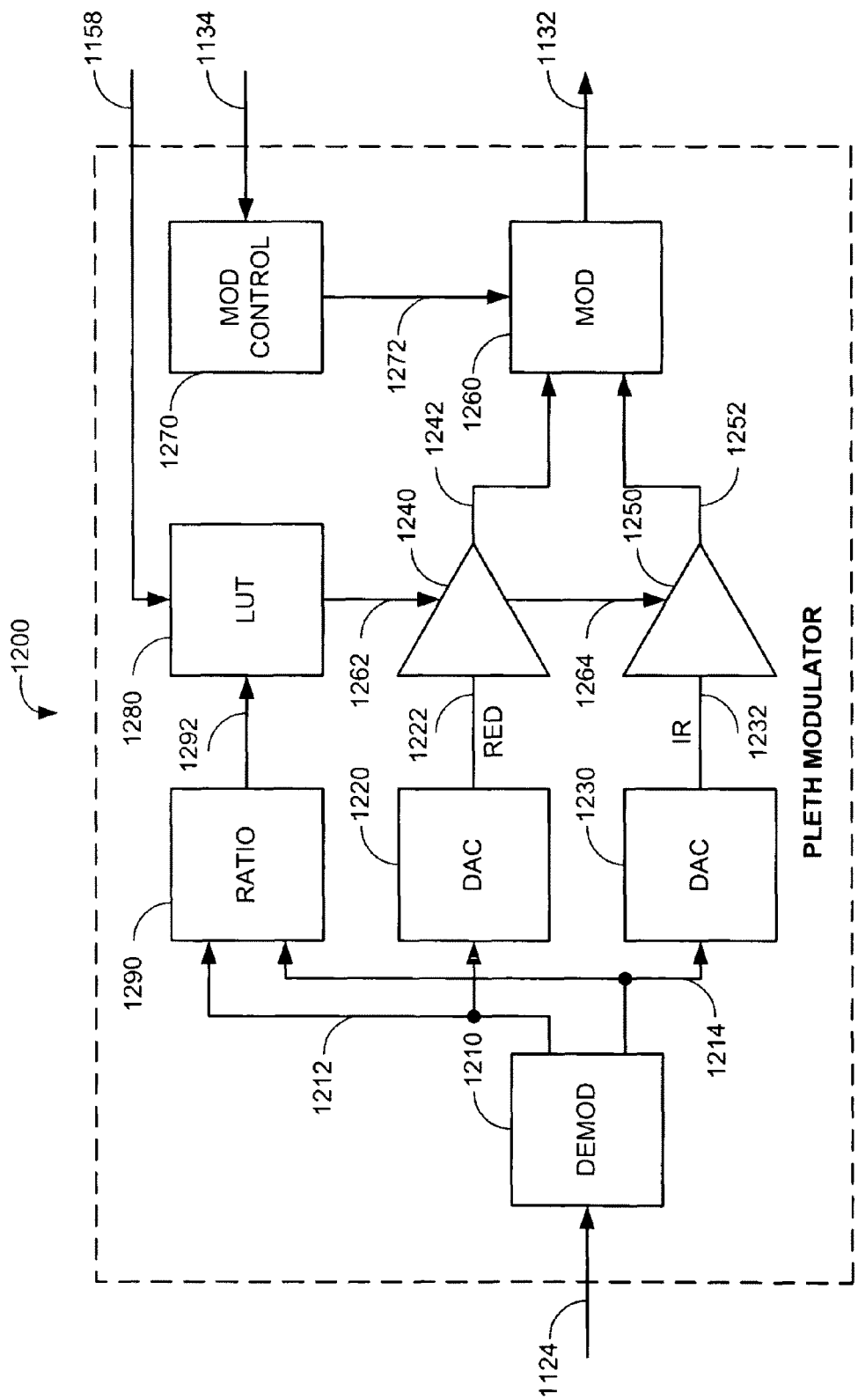
FIG. 12 is a functional block diagram of a waveform modulator.

FIG. 12 shows a waveform modulator 1200 having a demodulator 1210, a red digital-to-analog converter (DAC) 1220, an IR DAC 1230, a red amplifier 1240, an IR amplifier 1250, a modulator 1260, a modulator control 1270, a look-up table (LUT) 1280 and a ratio calculator 1290. The waveform modulator 1200 demodulates red and IR plethysmographs ("pleths") from the decoder output 1124 into a separate red pleth 1222 and IR pleth 1232. The waveform modulator 1200 also adjusts the amplitudes of the pleths 1222, 1232 according to stored calibration curves for the sensor 310 (FIG. 10) and the monitor 360 (FIG. 11). Further, the waveform modulator 1200 re-modulates the adjusted red pleth 1242 and adjusted IR pleth 1252, generating a modulated waveform 1132 to the monitor 360 (FIG. 11).

As shown in FIG. 12, the demodulator 1210 performs the demodulation function described above, generating digital red and IR pleth signals 1212, 1214. The DACs 1220, 1230 convert the digital pleth signals 1212, 1214 to corresponding analog pleth signals 1222, 1232. The amplifiers 1240, 1250 have variable gain control inputs 1262, 1264 and perform the amplitude adjustment function described above, generating adjusted red and IR pleth signals 1242, 1252. The modulator 1260 performs the re-modulation function described above, combining the adjusted red and IR pleth signals 1242, 1252 according to a control signal 1272. The modulator control 1270 generates the control signal 1272 synchronously with the LED drive signal(s) 1134 from the monitor 360.

Also shown in FIG. 12, the ratio calculator 1290 derives a red/IR ratio from the demodulator outputs 1212, 1214. The LUT 1280 stores empirical calibration data for the sensor 310 (FIG. 10). The LUT 1280 also downloads monitor-specific calibration data from the ROM 1160 (FIG. 11) via the ROM output 1158. From this calibration data, the LUT 1280 determines a desired red/IR ratio for the modulated waveform 1132 and generates red and IR gain outputs 1262, 1264 to the corresponding amplifiers 1240, 1250, accordingly. A desired red/IR ratio is one that allows the monitor 360 (FIG. 11) to derive oxygen saturation measurements from the modulated waveform 1132 that are generally equivalent to that derivable directly from the sensor signal 1012 (FIG. 10).

One of ordinary skill in the art will recognize that some of the signal processing functions described with respect to FIGS. 8-11 may be performed either within a sensor module or within a monitor module. Signal processing functions performed within a sensor module may advantageously reduce the transmission bandwidth to a monitor module at a cost of increased sensor module size and power consumption. Likewise, signal processing functions performed within a monitor module may reduce sensor module size and power consumption at a cost of increase transmission bandwidth.

For example, a monitor module embodiment 900 (FIG. 9) described above receives measured pulse oximeter parameters, such as oxygen saturation and pulse rate, and generates a corresponding synthesized waveform. In that embodiment, the oxygen saturation and pulse rate computations are performed within a sensor module 800 (FIG. 8). Another monitor module embodiment 1100 (FIG. 11), also described above, receives a plethysmograph waveform and generates a remodulated waveform. In that embodiment, minimal signal processing is performed within a sensor module 1000 (FIG. 10). In yet another embodiment, not shown, a sensor module transmits a plethysmograph waveform or a decimated plethysmograph waveform having a reduced sample rate. A corresponding monitor module has a signal processor, such as described with respect to FIG. 8, in addition to a waveform generator, as described with respect to FIG. 9. The signal processor computes pulse oximeter parameters and the waveform generator generates a corresponding synthesized waveform, as described above. In this embodiment, minimal signal processing is performed within the sensor module, and the monitor module functions are performed on the pulse oximeter parameters computed within the monitor module.

Wireless Multiple Parameter Measurements

FIGS. 13-14 illustrate a multiple parameter communications adapter. FIG. 13 illustrates a multiple parameter sensor module 1300 having sensor interfaces 1310, one or more signal processors 1330, a multiplexer and encoder 1340, a transmitter 1350, a transmitting antenna 1370 and a controller 1390. One or more physiological sensors 1301 provide input sensor signals 1312 to the sensor module 1300. Depending on the particular sensors 1301, the sensor module 1300 may provide one or more drive signals 1312 to the sensors 1301 as determined by the controller 1390. The sensor interfaces 1310 input the sensor signals 1312 and output one or more conditioned signals 1314. The conditioned signals 1314 may be coupled to the transmitter 1350 or further processed by the signal processors 1330. If the sensor module configuration utilizes signal processors 1330, it derives multiple parameter signals 1332 responsive to the sensor signals 1312, which are then coupled to the transmitter 1350. Regardless, the transmitter 1350 inputs a baseband signal 1342 that is responsive to the sensor signals 1312. The transmitter 1350 modulates the baseband signal 1342 with a carrier to generate a transmit signal 1354, which is coupled to the transmit antenna 1370 and communicated to a corresponding receive antenna 1470 (FIG. 14), as described with respect to FIG. 6, above. Alternatively, there may be multiple baseband signals 1342, and the transmitter 1350 may transmit on multiple frequency channels, where each channel coveys data responsive to one or more of the sensor signals 1314.

As shown in FIG. 13, the sensor interface 1310 conditions and digitizes the sensor signals 1312 as described for a single sensor with respect to FIG. 6, above. The resulting conditioned signals 1314 are responsive to the sensor signals 1312. The signal processors 1330 perform signal processing on the conditioned signals 1314 to derive parameter signals 1332, as described for a single conditioned signal with respect to FIG. 6, above. The parameter signals 1332 may be physiological measurements such as oxygen saturation, pulse rate, blood glucose, blood pressure, EKG, respiration rate and body temperature to name a few, or may be intermediate results from which the above-stated measurements may be calculated or derived. The multiplexer and encoder 1340 combines multiple digital word or serial bit streams into a single digital word or bit stream. The multiplexer and encoder also encodes the digital word or bit stream to generate the baseband signal 1342, as described with respect to FIG. 6, above.

FIG. 14 illustrates a multiple parameter monitor module 1400 having a receive antenna 1470, a receiver 1410, a demultiplexer and decoder 1420, one or more waveform processors 1430 and a monitor interface 1450. The receiver 1410 inputs and demodulates the receive signal 1412 corresponding to the transmit signal 1354 (FIG. 13) to generate a baseband signal 1414 as described with respect to FIG. 7, above. The demultiplexer and decoder 1420 separates the symbol streams corresponding to the multiple conditioned signals 1314 (FIG. 13) and/or parameter signals 1332 (FIG. 13) and translates these symbol streams into multiple decoded signals 1422, as described for a single symbol stream with respect to FIG. 7, above. Alternatively, multiple frequency channels are received to generate multiple baseband signals, each of which are decoded to yield multiple decoded signals 1422. The waveform processors 1430 input the decoded signals 1422 and generate multiple constructed signals 1432, as described for a single decoded signal with respect to FIGS. 7-12, above. The monitor interface 1450 is configured to communicate the constructed signals 1432 to the sensor ports of a multiple parameter monitor 1401 or multiple single parameter monitors, in a manner similar to that for a single constructed signal, as described with respect to FIGS. 7-12, above. In particular, the constructed signals 1432 are adapted to the monitor 1401 so that measurements derived by the monitor 1401 from the constructed signals 1432 are generally equivalent to measurements derivable directly from the sensor signals 1312 (FIG. 13).

A physiological measurement communications adapter is described above with respect to wireless communications and, in particular, radio frequency communications. A sensor module and monitor module, however, may also communicate via wired communications, such as telephone, Internet or fiberoptic cable to name a few. Further, wireless communications can also utilize light frequencies, such as IR or laser to name a few.

A physiological measurement communications adapter has been disclosed in detail in connection with various embodiments. These embodiments are disclosed by way of examples only. One of ordinary skill in the art will appreciate many variations and modifications of a physiological measurement communications adapter within the scope of the claims that follow.

What is claimed is:

1. A wearable, portable physiological monitor configured to wirelessly transmit real time information regarding a plurality physiological parameters, the portable monitor comprising:
   a plurality of sensor ports positioned on a housing of the portable monitor and configured to provide respective wired interfaces with different respective physiological sensors of a plurality of physiological sensors, wherein:
      at least a first sensor port of the plurality of sensor ports is positioned on a side of the housing of the portable monitor such that, when the portable monitor is attached to an arm of a patient, a wired connection extending from the first sensor port to a first physiological sensor positioned on a digit of the patient follows a path to the digit of the patient that is substantially perpendicular to the side of the housing and avoids tangling of the wired connection;
   one or more processing devices configured to:
      receive, via the plurality of sensor ports, a plurality of signals from the plurality of physiological sensors, at least some of the plurality of signals including digital information, and at least some of the plurality of signals including analog information;
      cause to be displayed, on a display of the portable monitor, a plurality of physiological parameters values responsive to the plurality of signals;
      combine information indicative of the plurality of signals into a single digital word or bit stream; and
      encode the single digital word or bit stream to generate a baseband signal; and
   a transmitter configured to:
      modulate the baseband signal with a carrier to generate a transmit signal; and
      wirelessly transmit the transmit signal to a remote patient monitoring device configured to decode the signal and display, on a remote display, the plurality of physiological parameters values responsive to the plurality of signals.

2. The portable monitor of claim 1, wherein the one or more processing devices are further configured to:
   process, at least in part in the analog domain, at least a first signal of the plurality of signals to determine at least a first one or more of the plurality of physiological parameters values; and
   process, at least in part in the digital domain, at least a second signal of the plurality of signals to determine at least a second one or more of the plurality of physiological parameters values.

3. The portable monitor of claim 2, wherein the first signal is received via the first sensor port from the first physiological sensor.

4. The portable monitor of claim 3, wherein the first physiological sensor comprises a pulse oximetry sensor.

5. The portable monitor of claim 4, wherein the first one or more of the plurality of physiological parameters values comprises at least oxygen saturation and pulse rate.

6. The portable monitor of claim 2, wherein the one or more processing devices comprise:
   a multiplexer configured to combine the information indicative of the plurality of signals into the single digital word or bit stream; and
   an encoder configured to encode the single digital word or bit stream to generate the baseband signal.

7. The portable monitor of claim 6, wherein the baseband signal comprises a single signal.

8. The portable monitor of claim 6, wherein the baseband signal comprises multiple related signal components including at least one of: in-phase signals or quadrature signals.

9. The portable monitor of claim 6, wherein the transmitter is further configured to transmit on multiple frequency channels.

10. The portable monitor of claim 1, wherein the plurality of sensor ports comprise at least:
    a second sensor port configured to receive a signal from an EKG sensor arrangement; and
    a third sensor port configured to receive a signal from a blood pressure sensor arrangement.

11. The portable monitor of claim 10 further comprising:
    a plurality of sensor interfaces configured to receive the plurality of signals and initially process the plurality of signals, wherein:
       each of the plurality of sensor interfaces is associated with a respective sensor port of the plurality of sensor ports, and
       each of the plurality of sensor interfaces is configured to receive a signal from a respective physiological sensor of the plurality of physiological sensors.

12. The portable monitor of claim 1, wherein a face of the housing comprises a single user interface, and the face of the housing is viewable by a user when the portable monitor is attached to the arm of the patient.

13. The portable monitor of claim 12, wherein the single user interface comprises the display.

14. The portable monitor of claim 13, wherein the display is positioned centrally on the face of the housing.

15. The portable monitor of claim 14, wherein the display positioned on the face of the housing is sized such that the display covers more than half of a length of a shortest dimension of the face of the housing.

16. A battery-powered wearable physiological monitoring device configured to communicate with multiple types of sensor arrangements via a plurality of sensor interfaces, the wearable physiological monitoring device comprising:
    a plurality of sensor communication ports including:
       a first sensor communication port configured to provide wired communication with a first type of physiological sensor arrangement, wherein the first sensor port is positioned on the device such that a wire extending from the first sensor communication port to the first type of physiological sensor arrangement extends from the device along an axis perpendicular to a face of the device upon which the first sensor port is positioned;
       a second sensor communication port configured to provide wired communication with a second type of physiological sensor arrangement different from the first type of physiological sensor arrangement; and
       a third sensor communication port configured to provide wired communication with a third type of physiological sensor arrangement different from both the first and second types of physiological sensor arrangements;
    a plurality of sensor interfaces including:

a first sensor interface configured to receive a first signal from a first sensor arrangement of the first type, the first signal including analog information;

a second sensor interface configured to receive a second signal from a second sensor arrangement of the second type the second signal including digital information; and a third sensor interface configured to receive a third signal from a third sensor arrangement of the third type;

wherein the plurality of sensor interfaces are configured to output one or more signals indicative of physiological parameters sensed by the first, second, and third sensor arrangements;

a display positioned on a face of the wearable physiological monitoring device configured to display information while the wearable physiological monitoring device is being worn by a patient;

a processor configured to:
responsive to the one or more signals indicative of the physiological parameters, cause to be displayed, on the display, physiological parameter measurements;
combine information indicative of the one or more signals into a single digital word or bit stream; and
encode the single digital word or bit stream to generate a baseband signal;

a transmitter configured to:
modulate the baseband signal with a carrier to generate a transmit signal; and
wirelessly transmit the transmit signal to a receiving patient monitoring device that is not wired to the wearable physiological monitoring device; and a battery configured to provide power to at least the processor, the display, the transmitter, and the first sensor arrangement via the first sensor communication port such that the wearable physiological monitoring device is portable and wearable by a patient.

17. The wearable physiological monitoring device of claim 16, wherein:
at least one of the first, second, or third sensor interfaces is configured to process signals at least in part in the analog domain; and
at least at different one of the first, second, or third sensor interfaces is configured to process signals at least in part in the digital domain.

18. The wearable physiological monitoring device of claim 17, wherein the first sensor arrangement comprises a pulse oximetry sensor configured to be attached to a digit of a patient.

19. The wearable physiological monitoring device of claim 18, wherein the first sensor port is positioned on a side of the wearable physiological monitoring device that faces a hand of a patient when the wearable physiological monitoring device is attached to an arm of the hand of the patient.

20. The wearable physiological monitoring device of claim 19, wherein the face of the wearable physiological monitoring device comprises a single user interface, and the single user interface comprises the display.

* * * * *

(12) INTER PARTES REVIEW CERTIFICATE (2590th)
United States Patent
Al-Ali

(10) Number: US 9,795,300 K1
(45) Certificate Issued: Feb. 16, 2022

(54) WEARABLE PORTABLE PATIENT MONITOR

(71) Applicant: Ammar Al-Ali

(72) Inventor: Ammar Al-Ali

(73) Assignee: MASIMO CORPORATION

Trial Number:

IPR2020-01015 filed May 29, 2020

Inter Partes Review Certificate for:

Patent No.: 9,795,300
Issued: Oct. 24, 2017
Appl. No.: 15/499,716
Filed: Apr. 27, 2017

The results of IPR2020-01015 are reflected in this inter partes review certificate under 35 U.S.C. 318(b).

INTER PARTES REVIEW CERTIFICATE
U.S. Patent 9,795,300 K1
Trial No. IPR2020-01015
Certificate Issued Feb. 16, 2022

AS A RESULT OF THE INTER PARTES REVIEW PROCEEDING, IT HAS BEEN DETERMINED THAT:

Claims 1-20 are cancelled.

\* \* \* \* \*